US011717567B2

(12) United States Patent
Oh et al.

(10) Patent No.: US 11,717,567 B2
(45) Date of Patent: *Aug. 8, 2023

(54) VACCINES AGAINST HPV AND HPV-RELATED DISEASES

(71) Applicant: BAYLOR RESEARCH INSTITUTE, Dallas, TX (US)

(72) Inventors: SangKon Oh, Baltimore, MD (US); Sandra Zurawski, Midlothian, TX (US); Gerard Zurawski, Midlothian, TX (US)

(73) Assignee: Baylor Research Institute, Dallas, TX (US)

( * ) Notice: Subject to any disclaimer, the term of this patent is extended or adjusted under 35 U.S.C. 154(b) by 116 days.

This patent is subject to a terminal disclaimer.

(21) Appl. No.: 17/194,779

(22) Filed: Mar. 8, 2021

(65) Prior Publication Data

US 2021/0268097 A1   Sep. 2, 2021

Related U.S. Application Data

(63) Continuation of application No. 16/397,214, filed on Apr. 29, 2019, now Pat. No. 10,940,195, which is a continuation of application No. 15/111,357, filed as application No. PCT/US2015/011236 on Jan. 13, 2015, now Pat. No. 10,286,058.

(60) Provisional application No. 62/002,718, filed on May 23, 2014, provisional application No. 61/926,821, filed on Jan. 13, 2014.

(51) Int. Cl.
| | |
|---|---|
| A61K 39/12 | (2006.01) |
| A61K 39/395 | (2006.01) |
| C07K 14/025 | (2006.01) |
| C07K 16/28 | (2006.01) |
| C07K 14/005 | (2006.01) |
| C12N 7/00 | (2006.01) |
| A61K 39/00 | (2006.01) |

(52) U.S. Cl.
CPC ............ *A61K 39/12* (2013.01); *A61K 39/395* (2013.01); *A61K 39/3955* (2013.01); *A61K 39/39541* (2013.01); *C07K 14/005* (2013.01); *C07K 16/2878* (2013.01); *C12N 7/00* (2013.01); *A61K 2039/505* (2013.01); *A61K 2039/53* (2013.01); *A61K 2039/55511* (2013.01); *A61K 2039/585* (2013.01); *A61K 2039/6056* (2013.01); *A61K 2039/70* (2013.01); *C07K 2317/24* (2013.01); *C07K 2317/56* (2013.01); *C07K 2317/565* (2013.01); *C07K 2319/74* (2013.01); *C07K 2319/91* (2013.01); *C12N 2710/20034* (2013.01)

(58) Field of Classification Search
None
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,578,770 | A | 3/1986 | Mitani |
| 4,599,230 | A | 7/1986 | Milich et al. |
| 4,599,231 | A | 7/1986 | Milich et al. |
| 4,601,903 | A | 7/1986 | Frasch |
| 4,608,251 | A | 8/1986 | Mia |
| 4,837,028 | A | 6/1989 | Allen |
| 4,902,505 | A | 2/1990 | Pardridge et al. |
| 4,957,735 | A | 9/1990 | Huang |
| 5,004,697 | A | 4/1991 | Pardridge |
| 5,019,369 | A | 5/1991 | Presant et al. |
| 5,055,303 | A | 10/1991 | Riley, Jr. |
| 5,188,837 | A | 2/1993 | Domb |
| 5,254,342 | A | 10/1993 | Shen et al. |
| 5,268,164 | A | 12/1993 | Kozarich et al. |
| 5,271,961 | A | 12/1993 | Mathiowitz et al. |
| 5,413,797 | A | 5/1995 | Khan et al. |
| 5,506,206 | A | 4/1996 | Kozarich et al. |

(Continued)

FOREIGN PATENT DOCUMENTS

| | | |
|---|---|---|
| AU | 2009/270771 | 1/2010 |
| CN | 1307484 | 8/2001 |

(Continued)

OTHER PUBLICATIONS

Harper et al. Review of Gardasil. J Vaccines Vaccin. Nov. 23, 2010; 1(107): 1000107.*
Attwood, "Genomics: The Babel of Bioinformatics" *Science* 2000, (290) 471-473.
Austyn et al., "Migration Patterns of Dendritic Cells in the Mouse" *J. Exp. Med.* 1988, (167) 646-651.
Banchereau et al., "Immunobiology of Dendritic Cells" *Annu. Rev. Immunol.* 2000, (18) 767-811.
Barrios-Marrugo, Kelly, "Therapeutic Peptide-Based Vaccination Strategies Against HPV-Induced Cancers," ProQuest LLC 2012.

(Continued)

*Primary Examiner* — Nianxiang Zou
(74) *Attorney, Agent, or Firm* — Norton Rose Fulbright US LLP

(57) ABSTRACT

Embodiments relate to novel vaccines against human papillomavirus (HPV) and HPV-related diseases, including multiple types of cancers. The HPV vaccines are composed of anti-human dendritic cell (DC) surface receptor antibodies, including CD40, and E6/7 proteins of HPV16 and 18. The technology described is not limited to making vaccines against HPV16- and HPV18-related diseases and can be applied to making vaccines carrying E6/7 from any type of HPV. The HPV vaccines described can target DCs, major and professional antigen presenting cells (APCs), and can induce and activate potent HPV E6/7-specific and strong CD4+ and CD8+ T cell responses. The HPV vaccines can be used for the prevention of HPV infection and HPV-related diseases as well as for the treatment of HPV-related diseases, including cancers.

22 Claims, 11 Drawing Sheets

Specification includes a Sequence Listing.

(56) References Cited

U.S. PATENT DOCUMENTS

| | | | |
|---|---|---|---|
| 5,514,670 A | 5/1996 | Friedman et al. |
| 5,534,496 A | 7/1996 | Lee et al. |
| 5,545,806 A | 8/1996 | Lonberg et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,770,429 A | 6/1998 | Lonberg et al. |
| 5,871,746 A | 2/1999 | Boutillon et al. |
| 6,140,059 A | 10/2000 | Shawaller |
| 6,469,143 B2 | 10/2002 | Sallberg |
| 6,541,011 B2 | 4/2003 | Punnonen et al. |
| 6,573,245 B1 | 6/2003 | Marciani |
| 7,060,495 B2 | 6/2006 | Gehrmann et al. |
| 7,067,110 B1 | 6/2006 | Gillies et al. |
| 7,118,751 B1 | 10/2006 | Ledbetter et al. |
| 7,122,187 B2 | 10/2006 | Black et al. |
| 7,261,897 B2 | 8/2007 | Skeiky et al. |
| 7,288,251 B2 | 10/2007 | Bedian et al. |
| 7,456,260 B2 | 11/2008 | Rybak et al. |
| 7,476,386 B1 | 1/2009 | Gras-Masse et al. |
| 7,560,534 B2 | 7/2009 | Deo et al. |
| 8,518,410 B2 | 8/2013 | Zurawski et al. |
| 8,961,991 B2 | 2/2015 | Zurawski et al. |
| 9,102,734 B2 | 8/2015 | Zurawski et al. |
| 9,109,011 B2 | 8/2015 | Banchereau et al. |
| 2002/0025513 A1 | 2/2002 | Sallberg |
| 2004/0001853 A1 | 1/2004 | George et al. |
| 2004/0110226 A1 | 6/2004 | Lazar et al. |
| 2004/0120948 A1 | 6/2004 | Mikayama et al. |
| 2004/0146948 A1 | 7/2004 | Britton et al. |
| 2005/0013828 A1 | 1/2005 | George et al. |
| 2005/0221295 A1 | 10/2005 | Hu et al. |
| 2006/0165690 A1 | 7/2006 | Heath et al. |
| 2006/0246089 A1 | 11/2006 | Wu et al. |
| 2007/0025982 A1 | 2/2007 | Ledbetter et al. |
| 2007/0148163 A1 | 6/2007 | Takahashi et al. |
| 2008/0181915 A1 | 7/2008 | Tripp et al. |
| 2008/0199471 A1 | 8/2008 | Bernett et al. |
| 2008/0226667 A1 | 9/2008 | Medzhitov |
| 2008/0233083 A1 | 9/2008 | Ansari et al. |
| 2008/0241139 A1 | 10/2008 | Delucia |
| 2008/0241170 A1 | 10/2008 | Zurawski et al. |
| 2008/0254026 A1 | 10/2008 | Long et al. |
| 2009/0004194 A1 | 1/2009 | Kedl |
| 2009/0068214 A1 | 3/2009 | Qian et al. |
| 2009/0238822 A1 | 9/2009 | George et al. |
| 2009/0305979 A1* | 12/2009 | Sung ............... A61P 37/04 536/23.4 |
| 2009/0324491 A1 | 12/2009 | Aburatani et al. |
| 2009/0324538 A1 | 12/2009 | Wong et al. |
| 2010/0135994 A1 | 6/2010 | Banchereau et al. |
| 2010/0239575 A1 | 9/2010 | Banchereau et al. |
| 2010/0291082 A1 | 11/2010 | Zurawski et al. |
| 2010/0297114 A1 | 11/2010 | Zurawski et al. |
| 2010/0322929 A1* | 12/2010 | Zurawski ....... A61K 39/001129 435/69.6 |
| 2011/0274653 A1 | 11/2011 | Banchereau et al. |
| 2011/0311525 A1 | 12/2011 | Herbert-Fransen et al. |
| 2012/0039916 A1 | 2/2012 | Zurawski et al. |
| 2012/0231023 A1 | 9/2012 | Zurawski et al. |
| 2012/0244155 A1 | 9/2012 | Lecine et al. |
| 2012/0276148 A1 | 11/2012 | Deisseroth et al. |

FOREIGN PATENT DOCUMENTS

| | | |
|---|---|---|
| CN | 1582165 | 2/2005 |
| CN | 1198647 | 4/2005 |
| CN | 1646566 | 7/2005 |
| CN | 102770457 | 11/2012 |
| EP | 0491628 | 6/1992 |
| EP | 0239400 | 8/1994 |
| EP | 0438474 | 5/1996 |
| EP | 0463151 | 6/1996 |
| EP | 0546073 | 9/1997 |
| EP | 1391464 | 2/2004 |
| GB | 2405873 | 3/2005 |
| JP | H10/504458 | 5/1998 |
| JP | 2004/192125 | 7/2004 |
| JP | 2005/527513 | 9/2005 |
| JP | 2006/501131 | 1/2006 |
| JP | 2006/342173 | 12/2006 |
| JP | 2007/026135 | 2/2007 |
| JP | 2009/022289 | 2/2009 |
| JP | 2009/259188 | 11/2009 |
| JP | 2011-502486 | 1/2011 |
| JP | 2012-501323 | 1/2012 |
| JP | 2012/520074 | 9/2012 |
| JP | 2012-525410 | 10/2012 |
| JP | 2015/028021 | 2/2015 |
| WO | WO 88/01649 | 3/1988 |
| WO | WO 90/07861 | 7/1990 |
| WO | WO 95/06480 | 3/1995 |
| WO | WO 99/22008 | 5/1999 |
| WO | WO 99/27954 | 6/1999 |
| WO | WO 00/000156 | 1/2000 |
| WO | WO 2000/075348 | 12/2000 |
| WO | WO 2001/032714 | 5/2001 |
| WO | WO 2001/083755 | 11/2001 |
| WO | WO 2001/085798 | 11/2001 |
| WO | WO 2002/028905 | 4/2002 |
| WO | WO 2003/024480 | 3/2003 |
| WO | WO 2003/029296 | 4/2003 |
| WO | WO 2003/040169 | 5/2003 |
| WO | WO 2004/035619 | 4/2004 |
| WO | WO 2004/069873 | 8/2004 |
| WO | WO 2004/076489 | 9/2004 |
| WO | WO 2006/128103 | 11/2006 |
| WO | WO 2007/041861 | 4/2007 |
| WO | WO 2007/051169 | 5/2007 |
| WO | WO 2007/130493 | 11/2007 |
| WO | WO 2008/047723 | 4/2008 |
| WO | WO 2008/097817 | 8/2008 |
| WO | WO 2008/097870 | 8/2008 |
| WO | WO 2008/103947 | 8/2008 |
| WO | WO 2008/118587 | 10/2008 |
| WO | WO 2010/009346 | 1/2010 |
| WO | WO 2010/104747 | 9/2010 |
| WO | WO 2010/104748 | 9/2010 |
| WO | WO 2010/104749 | 9/2010 |
| WO | WO 2010/104761 | 9/2010 |
| WO | WO 2011/023785 | 3/2011 |
| WO | WO 2011/032161 | 3/2011 |
| WO | WO 2011/140255 | 11/2011 |
| WO | WO 2012/021834 | 2/2012 |
| WO | WO 2013/028996 | 2/2013 |
| WO | WO 2013/092875 | 6/2013 |
| WO | WO 2012/029802 | 10/2013 |

OTHER PUBLICATIONS

Bates et al., "APCs Express DCIR, a Novel C-Type Lectin Surface Receptor Containing an Immunoreceptor Tyrosine-Based Inhibitory Motif" *J. Immunol.* 1999, (163) 1973-1983.

Beauchamp et al., "A New Procedure for the Synthesis of Polyethylene Glycol-Protein Adducts; Effects on Function, Receptor Recognition, and Clearance of Superoxide Dismutase, Lactoferrin, and a2-Macroglobulin" *Analytical Biochemistry* 1983, (131) 25-33.

Benton et al., "The Use of UCOE Vectors in Combination with a Preadapted Serum Free, Suspension Cell Line Allows for Rapid Production of Large Quantities of Protein" *Cytotechnology* 2002, (38) 43-46.

Bonifaz et al., "Efficient Targeting of Protein Antigen to the Dendritic Cell Receptor DEC-205 in the Stead State Leads to Antigen Presentation on major Histocompatibility Complex Class I Products and Peripheral CD8+ T Cell Tolerance" *The Journal of Experimental Medicine* 2002, 12(196) 1627-1638.

Carlring et al., "CD40 antibody as an adjuvant induces enhanced T cell responses" *Vaccine* 2004, (22) 3323-3328.

(56) References Cited

OTHER PUBLICATIONS

Chen et al., "Enhancement and destruction of antibody function by somatic mutation: unequal occurrence is controlled by V gene combinatorial associations." *The EMBO Journal* 1995, 12(14) 2784-2794.
Colman, "Effects of amino acid sequence changes on antibody-antigen interactions" *Research in Immunology* 1994, (145) 33-36.
Connick et al., "CTL fail to accumulate at sites of HIV-1 replication in lymphoid tissue" *Journal of Immunology* 2007; (178) 3978-683.
Cruz et al., "Process development of a recombinant antibody/interleukin-2 fusion protein expressed in protein-free medium by BHK cells" *Journal of Biotechnology* 2002, 2(96) 169-183.
Dakappagari et al., "Internalizing antibodies to the C-Type lectins, L-SIGN and DC-SIGN, inhibit viral glycoprotein binding and deliver antigen to human dendritic cells for the induction of T Cell responses" *The Journal of Immunology* 2006, (176) 426-440.
Diehl et al. "CD40 activation in vivo overcomes peptide-induced peripheral cytotoxic T-lymphocyte tolerance and augments anti-tumor vaccine efficacy" *Nature Medicine* 5(7):774-779. 1999.
Durier et al., "Clinical Safety of HIV Lipopeptides used as vaccines in healthy volunteers and HIV-infected adults," *AIDS* 2006, 20(7),1039-49.
Dye et al., "Global Burden of Tuberculosis—Estimated Incidence, Prevalence, and Mortality by Country" *JAMA* 1999, (282)677-686.
European Search Report issued in European Patent Application No. EP20150735460 dated Feb. 6, 2017.
Extended European Search Report issued in Application No. 17153786, dated Jul. 26, 2017.
Finn, "Cancer Vaccines: Between the Idea and the Reality" *Nature Reviews Immunology* 2003, (3) 630-641.
Fredriksen, et al., "DNA Vaccines Increase Immunogenicity of Idiotypic Tumor Antigen by Targeting Novel Fusion Proteins to Antigen-Presenting Cells," *Molecular Therapy: The Journal of the American Society of Gene Therapy* 2006, 13(4); 776-785.
French et al., "CD40 antibody evokes a cytotoxic T-cell response that eradicates lymphoma and bypasses T-cell help" *Nature Medicine* 1999, 5(5) 548-553.
Gallo, R., "The end or the beginning of the drive to an HIV-preventative vaccine: a view from over 20 years" *The Lancet* 2005; (366) 1894-1898.
Grossman et al., "Enhancement of the Priming Efficacy of DNA Vaccines Encoding Dendritic Cell-Targeted Antigens by Synergistic Toll-Like Receptor Ligands" *BMC Immunology* 2009, 10:43 1-10.
Hougardy et al., "Heparin-Binding-Hemagglutinin-Induced IFN-y Release as a Diagnostic Tool for Latent Tuberculosis" *PLOS One* 2007, 10 8 pages.
Hung et al., "Therapeutic human papillomavirus vaccines: current clinical trials and future direction," *Expert Opin Biol Ther*, 8(4): pp. 421-439, 2008.
Ihara, "Human Papillomavirus and Cervical Cancer—From Molecular Biology of HPV to HPV Vaccination," *Modem Media* 2007, 53(5); 115-121.
International Search Report and Written Opinion for PCT/US2010/026375 prepared by Korean Intellectual Property Office, dated Nov. 19, 2010.
International Search Report and Written Opinion for PCT/US2010/026268 prepared by Korean Intellectual Property Office, dated Dec. 31, 2010.
International Search Report and Written Opinion for PCT/US2010/026273 prepared by Korean Intellectual Property Office, dated Jan. 9, 2011.
International Search Report and Written Opinion for PCT/US2010/026275 prepared by Korean Intellectual Property Office, dated Jan. 7, 2011.
International Search Report and Written Opinion Issued in International Application No. PCT/US2015/011236, dated Apr. 6, 2015.
International Search Report for PCT/US2012/030593, dated May 28, 2012.
Keler et al., "Antibody-targeted vaccines" *Oncogene* 2007, 26(25) 3758-3767.
Klinguer et al., "Characterization of a multi-lipopeptides mixture used as an HIV-I vaccine candidate" *Vaccine* 2000, (18) 259-267.
Kussie et al., "A single engineered amino acid substitution changes antibody fine specificity." *J. Immunol* 1994, (152) 146-152.
Langer, "Polymer-Controlled Drug Delivery Systems" *Ace. Chem. Res.* 1993, (26) 537-542.
Levine, A., "Why do we not yet have a human immunodeficiency virus vaccine?" *Journal of Virology* 2008; 82(24): 11998-12000.
Li, "Synergistic Antibody Induction by Antigen-CD40 Ligand Fusion Protein as Improved Immunogen" *Immunology* 2005, (115) 215-222.
Liu et al. "Advances in peptide-based Human Papillomavirus Therapeutic Vaccines" *Current Topics in Medicinal Chemistry*, 12: pp. 1581-1592, 2012.
Lo-Man et al., "Anti-tumor immunity provided by a synthetic multiple antigenic glycopeptide displaying a Tri-Tn glycotope" *The Journal of Immunology* 2001, (166) 2849-2854.
Mariani et al., "HPV vaccine: an overview of immune response, clinical protection, and new approaches for the future" *Journal of Translational Medicine* 2010, 8:105 1-8.
Melero et al., "Immunostimulatory monoclonal antibodies for cancer therapy," *Nat. Rev. Cancer* 2007; (7) 95-106.
Nonn et al. "Dendritic cell-based tumor vaccine for cervical cancer I: in vitro stimulation with recombinant protein-pulsed dendritic cells induces specific T cells to HPV16 E7 or HPV18 E7" *J Cancer Res Clin Oncol* 129, 511-520, 2003.
Office Action issued in corresponding Canadian Patent Application No. 2,754,743, dated Jan. 10, 2018.
Office Action Issued in Corresponding Chinese Application No. 2016100873149, dated Feb. 11, 2019.
Office Action issued in corresponding Chinese patent application No. 201580013480, dated Apr. 2, 2019 (No translation available).
Office Action Issued in Corresponding European Application No. 17153786.3, dated Aug. 17, 2018.
Office Action issued in Japanese Application No. 2016-198376, dated Aug. 3, 2017.
Office Action Issued in Japanese Application No. 2017-007783, dated Nov. 20, 2018.
Paquette et al., "Interferon-alpha induces dendritic cell differentiation of CML mononuclear cells in vitro and in vivo" *Leukemia* 2002, (16) 1484-1489.
Reddy et al., "Elimination of Fc Receptor-Dependent Effector Functions of a Modified IgG4 Monoclonal Antibody to Human CD4" *The Journal of Immunology* 2000, (164) 1925-1933.
Rescigno et al., "Bacteria-induced neo-biosynthesis, stabilization, and surface expression of functional class 1 molecules in mouse dendritic cells" *Proc. Nail. Acad. Sci.* 1998, (95) 5229-5234.
Rudikoff et al., "Single amino acid substitution altering antigen-binding specificity" *Proc. Nat. Acad. Sci. USA* 1982, (79) 1979-1983.
Schjetne et al., "Delivery of Antigen to CD40 Induces Protective Immune Responses against Tumors" *The Journal of Immunology* 2007, 178(7) 4169-4176.
Schuurhuis et al., "Immature Dendritic Cells Acquire CDS+ Cytotoxic T Lymphocyte Priming Capacity upon Activation by T Helper Cell-independent of-dependent Stimuli" *J. Exp. Med.* 2000, (192) 145-150.
Search Report Issued in Corresponding Chinese Application No. 2016100873149, dated Jan. 29, 2019.
Skolnick et al., "From genes to protein structure and function: novel applications of computational approaches in the genomic era" *Trends in Biotech.* 2000, (18) 34-39.
Soares et al., "Three different vaccines based on the 140-amino acid MUC1 peptide with seven tandemly repeated tumor-specific epitopes elicit distinct immune effector mechanisms in wild-type versus MUC1-Transgenic mice with different potential for tumor rejection" *The Journal of Immunology* 2001, (166) 6555-6563.
Spitler, "Cancer Vaccines: The Interferon Analogy" *Cancer Biotherapy* 1995, (10) 1-3.
Steinman, "The Dendritic Cell System and its Role in Immunogenicity" *Annual Review Immunology* 1991, (9) 271-296.

(56) References Cited

OTHER PUBLICATIONS

Stork et al., "N-Glycosylation as Novel Strategy to Improve Pharmacokinetic Properties of Bispecific Single-chain Diabodies" 2008, 12(283) 7804-7812.

Tacken et al., "Dendritic-cell immunotherapy: from ex vivo loading to in vivo targeting" *Nature Reviews* 2007, 10(7) 790-802.

Trumpfheller et al., "Intensified and protective CD4+ T cell immunity in mice with anti-dendritic cell HIV gag fusion antibody vaccine" *The Journal of Experimental Medicine* 2006, 3(203) 607-617.

Van Vliet et al., "Dendritic Cells and C-Type Lectin Receptors: Coupling Innate to Adaptive Immune Responses" *Immunology and Cell Biology* 2008, (86) 580-587.

Vonderhelde et al., "Agonistic CD40 antibodies and cancer therapy" *Clin Cancer Res* 2013, (19) 1035-1043.

Walker et al. "Toward an AIDS vaccine" *Science*, 2008; (320) 760-764.

Wells et al., "Combined Triggering of Dendritic Cell Receptors Results in Synergistic Activation and Potent Cytotoxic Immunity," *J. Immunol.* 2008; (181) 3422-3431.

Winter et al., "Antibody-based therapy" *Immunology Today* 1993, 6(14).

Xiang et al., "A Dual-Function DNA Vaccine Encoding Carcinoembryonic Antigen and CD40 Ligand Trimer Induces T Cell-Mediated Protective Immunity Against Colon Cancer in Carcinoembryonic Antigen-Transgenic Mice," *J. Immunol.* 2001; (167); pp. 4560-4565.

Xiong et al., "Expression of B-Cell Naturation Antigen mRNA in Peripheral Blood Mononuclear Cells in Patients with Systemic Lupus Erythematosus" *Huaxi Yixue* 2010, 1 page (Abstract Only).

Zhang et al., "An Adenoviral Vector Cancer Vaccine that Delivers a Tumor-Associated Antigen/CD40-Ligand Fusion Protein to Dendritic Cells" *PNAS 2003*, 25(100) 15101-15106.

\* cited by examiner

SEQUENCE LISTING

<160> NUMBER OF SEQ ID NOS: 31

<210> SEQ ID NO 1
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 1

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Gly Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Val Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu
        115                 120

<210> SEQ ID NO 2
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 2

Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
            20                  25                  30

```
Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys
        50                  55                  60

<210> SEQ ID NO 3
<211> LENGTH: 114
<212> TYPE: PRT
<213> ORGANISM: Artificial Sequence
<220> FEATURE:
<223> OTHER INFORMATION: Synthetic Peptide

<400> SEQUENCE: 3

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
            20                  25                  30

Val Tyr Cys Lys Thr Val Leu Glu Leu Thr Glu Val Gly Glu Phe Ala
        35                  40                  45

Phe Lys Asp Leu Phe Val Val Tyr Arg Asp Ser Ile Pro His Ala Ala
    50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro

<210> SEQ ID NO 4
<211> LENGTH: 67
<212> TYPE: PRT
<213> ORGANISM: Artificial Sequence
<220> FEATURE:
<223> OTHER INFORMATION: Synthetic Peptide

<400> SEQUENCE: 4

Met His Gly Pro Lys Ala Thr Leu Gln Asp Ile Val Leu His Leu Glu
1               5                   10                  15

Pro Gln Asn Glu Ile Pro Val Asp Leu Leu Gly His Gly Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
    50                  55                  60

Cys Cys Lys
65

<210> SEQ ID NO 5
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 5

Gln Thr Pro Thr Asn Thr Ile Ser Val Thr Pro Thr Asn Asn Ser Thr
1               5                   10                  15

Pro Thr Asn Asn Ser Asn Pro Lys Pro Asn Pro
            20                  25
```

<210> SEQ ID NO 6
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 6

```
Ser Ser Val Ser Pro Thr Thr Ser Val His Pro Thr Pro Thr Ser Val
1               5                   10                  15

Pro Pro Thr Pro Thr Lys Ser Ser Pro
            20                  25
```

<210> SEQ ID NO 7
<211> LENGTH: 214
<212> TYPE: PRT
<213> ORGANISM: Artificial Sequence
<220> FEATURE:
<223> OTHER INFORMATION: Synthetic Peptide

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Phe Asn Lys Leu Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 8
<211> LENGTH: 446
<212> TYPE: PRT
<213> ORGANISM: Artificial Sequence
<220> FEATURE:
<223> OTHER INFORMATION: Synthetic Peptide

<400> SEQUENCE: 8

-continued

```
Glu Val Lys Leu Val Glu Ser Gly Gly Gly Leu Val Gln Pro Gly Gly
1               5                   10                  15
Ser Leu Lys Leu Ser Cys Ala Thr Ser Gly Phe Thr Phe Ser Asp Tyr
            20                  25                  30
Tyr Met Tyr Trp Val Arg Gln Ala Pro Gly Lys Gly Leu Glu Trp Val
        35                  40                  45
Ala Tyr Ile Asn Ser Gly Gly Ser Thr Tyr Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Gly Leu Pro Phe His Ala Met Asp Tyr Trp Gly Gln Gly
            100                 105                 110
Thr Leu Val Thr Val Ser Ser Ala Lys Thr Lys Gly Pro Ser Val Phe
            115                 120                 125
Pro Leu Ala Pro Cys Ser Arg Ser Thr Ser Glu Ser Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
    210                 215                 220
Cys Pro Pro Cys Pro Ala Pro Glu Phe Glu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
```

```
                    420                 425                 430
Asn His Tyr Thr Gln Lys Ser Leu Ser Leu Ser Leu Gly Lys
        435                 440                 445

<210> SEQ ID NO 9
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Gly Asn Leu Glu Pro
65                  70                  75                  80

Glu Asp Ile Ala Thr Tyr Tyr Cys Gln Gln Phe Asn Lys Leu Pro Pro
                85                  90                  95

Thr Phe Gly Gly Gly Thr Lys Leu Glu Ile Lys
            100                 105

<210> SEQ ID NO 10
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 10

Cys Glu Val Lys Leu Val Glu Ser Gly Gly Gly Leu Val Gln Pro Gly
1               5                   10                  15

Gly Ser Leu Lys Leu Ser Cys Ala Thr Ser Gly Phe Thr Phe Ser Asp
            20                  25                  30

Tyr Tyr Met Tyr Trp Val Arg Gln Thr Pro Glu Lys Arg Leu Glu Trp
        35                  40                  45

Val Ala Tyr Ile Asn Ser Gly Gly Gly Ser Thr Tyr Tyr Pro Asp Thr
    50                  55                  60

Val Lys Gly Arg Phe Thr Ile Ser Arg Asp Asn Ala Lys Asn Thr Leu
65                  70                  75                  80

Tyr Leu Gln Met Ser Arg Leu Lys Ser Glu Asp Thr Ala Met Tyr Tyr
                85                  90                  95

Cys Ala Arg Arg Gly Leu Pro Phe His Ala Met Asp Tyr Trp Gly Gln
            100                 105                 110

Gly Thr Ser Val Thr Val Ser
        115

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 11
```

```
Ser Ala Ser Gln Gly Ile Ser Asn Tyr Leu Asn
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 12

Tyr Thr Ser Ile Leu His Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Gln Gln Phe Asn Lys Leu Pro Pro Thr
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 14

Gly Phe Thr Phe Ser Asp Tyr Tyr Met Tyr
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 15

Tyr Ile Asn Ser Gly Gly Gly Ser Thr Tyr Tyr Pro Asp Thr Val Lys
1               5                   10                  15

Gly

<210> SEQ ID NO 16
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 16

Arg Gly Leu Pro Phe His Ala Met Asp Tyr
1               5                   10

<210> SEQ ID NO 17
<211> LENGTH: 214
<212> TYPE: PRT
<213> ORGANISM: Artificial Sequence
<220> FEATURE:
<223> OTHER INFORMATION: Synthetic Peptide
```

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65              70                  75                  80

Glu Asp Phe Ala Thr Tyr Tyr Cys Gln Gln Phe Asn Lys Leu Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 705
<212> TYPE: DNA
<213> ORGANISM: Artificial Sequence
<220> FEATURE:
<223> OTHER INFORMATION: Synthetic Primer

<400> SEQUENCE: 18
atgagggtcc ccgctcagct cctggggctc ctgctgctct ggctcccagg cgcgcgatgt      60
gatatccaga tgacacagag cccttcctcc ctgtctgcct ctgtgggaga cagagtcacc     120
atcacctgca gtgcaagtca gggcattagc aattatttaa actggtatca gcagaaacca     180
ggcaaggccg ttaaactcct gatctattac acatcaattt tacactcagg agtcccatca     240
aggttcagtg gcagtgggtc tgggacagat tataccctca ccatcagctc cctgcagcct     300
gaagatttcg ccacttacta ttgtcagcag tttaataagc ttcctccgac gttcggtgga     360
ggcaccaaac tcgagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctatgcct gcgaagtcac ccatcagggc     660
ctgagctcgc ccgtcacaaa gagcttcaac aggggagagt gttag                     705

```
<210> SEQ ID NO 19
<211> LENGTH: 688
<212> TYPE: PRT
<213> ORGANISM: Artificial Sequence
<220> FEATURE:
<223> OTHER INFORMATION: Synthetic Peptide

<400> SEQUENCE: 19
```

| | | | | | | | | | | | | | | |
|---|---|---|---|---|---|---|---|---|---|---|---|---|---|---|
| Glu | Val | Lys | Leu | Val | Glu | Ser | Gly | Gly | Gly | Leu | Val | Gln | Pro | Gly |
| 1 | | | | 5 | | | | | 10 | | | | | 15 |
| Ser | Leu | Lys | Leu | Ser | Cys | Ala | Thr | Ser | Gly | Phe | Thr | Phe | Ser | Asp | Tyr |
| | | | 20 | | | | | 25 | | | | | 30 | | |
| Tyr | Met | Tyr | Trp | Val | Arg | Gln | Ala | Pro | Gly | Lys | Gly | Leu | Glu | Trp | Val |
| | | 35 | | | | | 40 | | | | | 45 | | | |
| Ala | Tyr | Ile | Asn | Ser | Gly | Gly | Gly | Ser | Thr | Tyr | Tyr | Pro | Asp | Thr | Val |
| | 50 | | | | | 55 | | | | | 60 | | | | |
| Lys | Gly | Arg | Phe | Thr | Ile | Ser | Arg | Asp | Asn | Ala | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Arg | Gly | Leu | Pro | Phe | His | Ala | Met | Asp | Tyr | Trp | Gly | Gln | Gly |
| | | | 100 | | | | | 105 | | | | | 110 | | |
| Thr | Leu | Val | Thr | Val | Ser | Ser | Ala | Lys | Thr | Lys | Gly | Pro | Ser | Val | Phe |
| | | 115 | | | | | 120 | | | | | 125 | | | |
| Pro | Leu | Ala | Pro | Cys | Ser | Arg | Ser | Thr | Ser | Glu | Ser | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Lys | Thr | Tyr | Thr | Cys | Asn | Val | Asp | His | Lys | Pro |
| | | 195 | | | | | 200 | | | | | 205 | | | |
| Ser | Asn | Thr | Lys | Val | Asp | Lys | Arg | Val | Glu | Ser | Lys | Tyr | Gly | Pro | Pro |
| | 210 | | | | | 215 | | | | | 220 | | | | |
| Cys | Pro | Pro | Cys | Pro | Ala | Pro | Glu | Phe | Glu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | Gln | Glu | Asp | Pro | Glu | Val |
| | | | 260 | | | | | 265 | | | | | 270 | | |
| Gln | Phe | Asn | Trp | Tyr | Val | Asp | Gly | Val | Glu | Val | His | Asn | Ala | Lys | Thr |
| | | 275 | | | | | 280 | | | | | 285 | | | |
| Lys | Pro | Arg | Glu | Glu | Gln | Phe | Asn | Ser | Thr | Tyr | Arg | Val | Val | Ser | Val |
| | 290 | | | | | 295 | | | | | 300 | | | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Gly | Leu | Pro | Ser | Ser | Ile | Glu | Lys | Thr | Ile | Ser |
| | | | | 325 | | | | | 330 | | | | | 335 | |
| Lys | Ala | Lys | Gly | Gln | Pro | Arg | Glu | Pro | Gln | Val | Tyr | Thr | Leu | Pro | Pro |
| | | | 340 | | | | | 345 | | | | | 350 | | |
| Ser | Gln | Glu | Glu | Met | Thr | Lys | Asn | Gln | Val | Ser | Leu | Thr | Cys | Leu | Val |
| | | 355 | | | | | 360 | | | | | 365 | | | |
| Lys | Gly | Phe | Tyr | Pro | Ser | Asp | Ile | Ala | Val | Glu | Trp | Glu | Ser | Asn | Gly |

```
            370                 375                 380
Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys Ala Ser
            435                 440                 445

Gln Thr Pro Thr Asn Thr Ile Ser Val Thr Pro Thr Asn Asn Ser Thr
450                 455                 460

Pro Thr Asn Asn Ser Asn Pro Lys Pro Asn Pro Ala Ser Met His Gln
465                 470                 475                 480

Lys Arg Thr Ala Met Phe Gln Asp Pro Gln Glu Arg Pro Arg Lys Leu
                485                 490                 495

Pro Gln Leu Cys Thr Glu Leu Gln Thr Thr Ile His Asp Ile Ile Leu
            500                 505                 510

Glu Cys Val Tyr Cys Lys Gln Gln Leu Leu Arg Arg Glu Val Gly Asp
            515                 520                 525

Phe Ala Phe Arg Asp Leu Cys Ile Val Tyr Arg Asp Gly Asn Pro Tyr
530                 535                 540

Ala Val Cys Asp Lys Cys Leu Lys Phe Tyr Ser Lys Ile Ser Glu Tyr
545                 550                 555                 560

Arg His Tyr Cys Tyr Ser Val Tyr Gly Thr Thr Leu Glu Gln Gln Tyr
                565                 570                 575

Asn Lys Pro Leu Cys Asp Leu Leu Ile Arg Cys Ile Asn Cys Gln Lys
            580                 585                 590

Pro Leu Cys Pro Glu Ala Ser Met His Gly Asp Thr Pro Thr Leu His
            595                 600                 605

Glu Tyr Met Leu Asp Leu Gln Pro Glu Thr Thr Asp Leu Tyr Gly Tyr
610                 615                 620

Gly Gln Leu Asn Asp Ser Ser Glu Glu Glu Asp Glu Ile Asp Gly Pro
625                 630                 635                 640

Ala Gly Gln Ala Glu Pro Asp Arg Ala His Tyr Asn Ile Val Thr Phe
                645                 650                 655

Cys Cys Lys Ala Ser Ser Ser Val Ser Pro Thr Thr Ser Val His Pro
            660                 665                 670

Thr Pro Thr Ser Val Pro Pro Thr Pro Thr Lys Ser Ser Pro Ala Ser
            675                 680                 685

<210> SEQ ID NO 20
<211> LENGTH: 2124
<212> TYPE: DNA
<213> ORGANISM: Artificial Sequence
<220> FEATURE:
<223> OTHER INFORMATION: Synthetic Primer

<400> SEQUENCE: 20
atgggttgga gcctcatctt gctcttcctt gtcgctgttg ctacgcgtgt ccactccgaa    60
gtgaagctgg tggagtctgg gggaggctta gtgcagcccg agggtccct gaaactctcc    120 tgtgcaacct ctggattcac tttcagtgac tattacatgt attgggttcg ccaggcccca    180
ggcaagggcc tggagtgggt cgcatacatt aattctggtg gtggtagcac ctattatcca    240
gacactgtaa agggccgatt caccatctcc agagacaatg ccaagaacac cctgtacctg    300
```

```
caaatgaaca gcctgagggc cgaggacaca gccgtgtatt actgtgcaag acggggggtta    360 ccgttccatg ctatggacta ttggggtcaa ggaaccctgg tcaccgtctc ctcagccaaa    420
acgaagggcc catccgtctt ccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcacgaa gacctacacc    660 tgcaacgtag atcacaagcc cagcaacacc aaggtggaca gagagttga gtccaaatat    720 ggtcccccat gcccaccctg cccagcacct gagttcgaag ggggaccatc agtcttcctg    780
ttccccccaa acccaaggac actctcatg atctcccgga ccctgaggt cacgtgcgtg    840 gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag    1020
gtctccaaca aaggcctccc gtcctccatc gagaaaacca tctccaaagc caaagggcag    1080
ccccgagagc cacaggtgta caccctgccc ccatcccagg aggagatgac caagaaccag    1140
gtcagcctga cctgcctggt caaaggcttc taccccagcg acatcgccgt ggagtgggag    1200
agcaatgggc agccggagaa caactacaag accacgcctc ccgtgctgga ctccgacggc    1260
tccttcttcc tctacagcag gctaaccgtg gacaagagca ggtggcagga ggggaatgtc    1320
ttctcatgct ccgtgatgca tgaggctctg cacaaccact acacacagaa gagcctctcc    1380
ctgtctctgg gtaaagctag tcagaccccc accaacacca tcagcgtgac ccccaccaac    1440
aacagcaccc ccaccaacaa cagcaacccc aagcccaacc ccgctagtat gcaccaaaaa    1500
aggaccgcaa tgtttcagga cccccaagag aggccccgca aactgccaca actttgcacg    1560
gagctgcaga caacaataca tgacatcatt ctcgaatgtg tttactgtaa gcagcagttg    1620
ttgcgaagag aagtgggaga cttcgctttc agagacctgt gtatcgtata tcgcgatggc    1680
aatccttatg ccgtctgcga taaatgcctc aagttttact ccaagatcag cgagtaccgg    1740
cactactgtt actctgtgta tgggactacc ctcgaacagc agtataacaa gccgctgtgc    1800
gatctcctta tccggtgcat taactgccag aagccactgt gtcctgaggc tagtatgcac    1860
ggggataccc ccacactcca cgaatacatg cttgatttgc aacctgaaac gaccgacctg    1920
tacggctatg gtcagctgaa tgactccagc gaggaagagg atgagattga cggaccggca    1980
ggccaggccg agccagaccg ggctcattat aacatcgtga ctttctgctg taaggctagt    2040
agcagcgtga gccccaccac cagcgtgcac cccaccccca ccagcgtgcc ccccaccccc    2100
accaagagca gccccgctag ctga                                           2124
```

<210> SEQ ID NO 21
<211> LENGTH: 689
<212> TYPE: PRT
<213> ORGANISM: Artificial Sequence
<220> FEATURE:
<223> OTHER INFORMATION: Synthetic Peptide

<400> SEQUENCE: 21

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Ala Pro Gly Lys Gly Leu Glu Trp Val

```
                35                  40                  45
Ala Tyr Ile Asn Ser Gly Gly Ser Thr Tyr Tyr Pro Asp Thr Val
 50                  55                  60
Lys Gly Arg Phe Thr Ile Ser Arg Asp Asn Ala Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Arg Gly Leu Pro Phe His Ala Met Asp Tyr Trp Gly Gln Gly
                100                 105                 110
Thr Leu Val Thr Val Ser Ser Ala Lys Thr Lys Gly Pro Ser Val Phe
                115                 120                 125
Pro Leu Ala Pro Cys Ser Arg Ser Thr Ser Glu Ser Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Lys Thr Tyr Thr Cys Asn Val Asp His Lys Pro
            195                 200                 205
Ser Asn Thr Lys Val Asp Lys Arg Val Glu Ser Lys Tyr Gly Pro Pro
210                 215                 220
Cys Pro Pro Cys Pro Ala Pro Glu Phe Glu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys Ala Ser
            435                 440                 445
Gln Thr Pro Thr Asn Thr Ile Ser Val Thr Pro Thr Asn Asn Ser Thr
            450                 455                 460
```

Pro Thr Asn Asn Ser Asn Pro Lys Pro Asn Pro Ala Ser Met Ala Arg
465                 470                 475                 480

Phe Glu Asp Pro Thr Arg Arg Pro Tyr Lys Leu Pro Asp Leu Cys Thr
            485                 490                 495

Glu Leu Asn Thr Ser Leu Gln Asp Ile Glu Ile Thr Cys Val Tyr Cys
        500                 505                 510

Lys Thr Val Leu Glu Leu Thr Glu Val Gly Glu Phe Ala Phe Lys Asp
            515                 520                 525

Leu Phe Val Val Tyr Arg Asp Ser Ile Pro His Ala Ala Cys His Lys
530                 535                 540

Cys Ile Asp Phe Tyr Ser Arg Ile Arg Glu Leu Arg His Tyr Ser Asp
545                 550                 555                 560

Ser Val Tyr Gly Asp Thr Leu Glu Lys Leu Thr Asn Thr Gly Leu Tyr
            565                 570                 575

Asn Leu Leu Ile Arg Cys Leu Arg Cys Gln Lys Pro Leu Asn Pro Ala
        580                 585                 590

Ser Met His Gly Pro Lys Ala Thr Leu Gln Asp Ile Val Leu His Leu
    595                 600                 605

Glu Pro Gln Asn Glu Ile Pro Val Asp Leu Leu Gly His Gly Gln Leu
610                 615                 620

Ser Asp Ser Glu Glu Asn Asp Glu Ile Asp Gly Val Asn His Gln
625                 630                 635                 640

His Leu Pro Ala Arg Arg Ala Glu Pro Gln Arg His Thr Met Leu Cys
            645                 650                 655

Met Cys Cys Lys Ala Ser Ser Ser Val Ser Pro Thr Thr Ser Val His
        660                 665                 670

Pro Thr Pro Thr Ser Val Pro Pro Thr Pro Thr Lys Ser Ser Pro Ala
    675                 680                 685

Ser

<210> SEQ ID NO 22
<211> LENGTH: 2127
<212> TYPE: DNA
<213> ORGANISM: Artificial Sequence
<220> FEATURE:
<223> OTHER INFORMATION: Synthetic Primer

<400> SEQUENCE: 22
atgggttgga gcctcatctt gctcttcctt gtcgctgttg ctacgcgtgt ccactccgaa     60
gtgaagctgg tggagtctgg gggaggctta gtgcagcccg agggtccct gaaactctcc    120 tgtgcaacct ctggattcac tttcagtgac tattacatgt attgggttcg ccaggcccca    180
ggcaagggcc tggagtgggt cgcatacatt aattctggtg gtgtagcac ctattatcca    240 gacactgtaa agggccgatt caccatctcc agagacaatg ccaagaacac cctgtacctg    300
caaatgaaca gcctgagggc cgaggacaca gccgtgtatt actgtgcaag acggggtta    360 ccgttccatg ctatggacta ttggggtcaa ggaaccctgg tcaccgtctc ctcagccaaa    420
acgaagggcc catccgtctt ccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct tgggcacgaa gacctacacc    660
tgcaacgtag atcacaagcc cagcaacacc aaggtggaca gagagttga gtccaaatat    720

| | |
|---|---|
| ggtcccccat gcccaccctg cccagcacct gagttcgaag ggggaccatc agtcttcctg | 780 |
| ttccccccaa aacccaagga cactctcatg atctcccgga cccctgaggt cacgtgcgtg | 840 |
| gtggtggacg tgagccagga agaccccgag gtccagttca actggtacgt ggatggcgtg | 900 |
| gaggtgcata atgccaagac aaagccgcgg gaggagcagt tcaacagcac gtaccgtgtg | 960 |
| gtcagcgtcc tcaccgtcct gcaccaggac tggctgaacg gcaaggagta caagtgcaag | 1020 |
| gtctccaaca aaggcctccc gtcctccatc gagaaaacca tctccaaagc caaagggcag | 1080 |
| ccccgagagc cacaggtgta caccctgccc ccatcccagg aggagatgac caagaaccag | 1140 |
| gtcagcctga cctgcctggt caaaggcttc taccccagcg acatcgccgt ggagtgggag | 1200 |
| agcaatgggc agccggagaa caactacaag accacgcctc ccgtgctgga ctccgacggc | 1260 |
| tccttcttcc tctacagcag gctaaccgtg gacaagagca ggtggcagga ggggaatgtc | 1320 |
| ttctcatgct ccgtgatgca tgaggctctg cacaaccact acacacagaa gagcctctcc | 1380 |
| ctgtctctgg gtaaagctag tcagaccccc accaacacca tcagcgtgac ccccaccaac | 1440 |
| aacagcaccc ccaccaacaa cagcaacccc aagcccaacc ccgctagtat ggccagattc | 1500 |
| gaggatccaa cacgccgacc ttacaaattg ccggaccttt gcacggagct gaacacttcc | 1560 |
| ctgcaggaca tagaaattac ctgcgtctac tgcaagacct tctcgaact gacagaagta | 1620 |
| ggcgagtttg cgtttaaaga tctgttcgtg gtgtatcggg atagcattcc ccacgcagct | 1680 |
| tgtcataagt gtatcgactt ctattctagg atccgggagc tcagacacta tagcgattcc | 1740 |
| gtgtacggcg acacacttga gaagctcact aacaccgggc tgtacaacct cctgatccgg | 1800 |
| tgcttgaggt gtcagaaacc cctgaatcct gctagtatgc acgggcctaa ggccacactg | 1860 |
| caagatattg tcctccatct cgaaccccag aatgagatac cagtggacct tctgggccac | 1920 |
| ggacagttgt ccgatagcga ggaggaaaac gacgaaatcg acggtgttaa ccaccagcac | 1980 |
| ttgccggctc ggagggcaga gccccagaga cataccatgc tgtgcatgtg ttgcaaagct | 2040 |
| agtagcagcg tgagccccac caccagcgtg caccccaccc ccaccagcgt gccccccacc | 2100 |
| cccaccaaga gcagccccgc tagctga | 2127 |

<210> SEQ ID NO 23
<211> LENGTH: 242
<212> TYPE: PRT
<213> ORGANISM: Artificial Sequence
<220> FEATURE:
<223> OTHER INFORMATION: Synthetic Peptide

<400> SEQUENCE: 23

```
Met Lys Lys Leu Leu Ile Ala Ala Met Met Ala Ala Ala Leu Ala Ala
1               5                   10                  15

Cys Ser Gln Glu Ala Lys Gln Glu Val Lys Glu Ala Val Gln Ala Val
            20                  25                  30

Glu Ser Asp Val Lys Asp Thr Ala Met Gly Ser Ser His His His His
        35                  40                  45

His His Ser Ser Gly Leu Val Pro Arg Gly Ser His Met Ala Ser Met
    50                  55                  60

Asp Leu Asp Ala Val Arg Ile Lys Val Asp Thr Val Asn Ala Lys Pro
65                  70                  75                  80

Gly Asp Thr Val Asn Ile Pro Val Arg Phe Ser Gly Ile Pro Ser Lys
                85                  90                  95

Gly Ile Ala Asn Cys Asp Phe Val Tyr Ser Tyr Asp Pro Asn Val Leu
            100                 105                 110
```

```
Glu Ile Ile Glu Ile Lys Pro Gly Glu Leu Ile Val Asp Pro Asn Pro
            115                 120                 125

Thr Lys Ser Phe Asp Thr Ala Val Tyr Pro Asp Arg Lys Met Ile Val
130                 135                 140

Phe Leu Phe Ala Glu Asp Ser Gly Thr Gly Ala Tyr Ala Ile Thr Lys
145                 150                 155                 160

Asp Gly Val Phe Ala Thr Ile Val Ala Lys Val Lys Glu Gly Ala Pro
                165                 170                 175

Asn Gly Leu Ser Val Ile Lys Phe Val Glu Val Gly Gly Phe Ala Asn
            180                 185                 190

Asn Asp Leu Val Glu Gln Lys Thr Gln Phe Phe Asp Gly Gly Val Asn
        195                 200                 205

Val Gly Asp Thr Thr Glu Pro Ala Thr Pro Thr Thr Pro Val Thr Thr
    210                 215                 220

Pro Thr Thr Thr Asp Asp Leu Asp Ala Ala Ser Leu Ile Lys Thr Ser
225                 230                 235                 240

Glu Phe

<210> SEQ ID NO 24
<211> LENGTH: 729
<212> TYPE: DNA
<213> ORGANISM: Artificial Sequence
<220> FEATURE:
<223> OTHER INFORMATION: Synthetic Primer

<400> SEQUENCE: 24
atgaaaaaac tgctgattgc cgccatgatg gctgcagctc tggccgcatg cagccaggaa      60
gccaaacagg aagtgaaaga agccgtgcag gccgtggaaa gcgatgtgaa agataccgcc     120
atgggcagca gccatcatca tcatcatcac agcagcggcc tggtgccgcg cggcagccat     180
atggctagta tggatctgga tgcagtaagg attaaagtgg acacagtaaa tgcaaaaccg     240
ggagacacag taaatatacc tgtaagattc agtggtatac catccaaggg aatagcaaac     300
tgtgactttg tatacagcta tgacccgaat gtacttgaga atagagatat aaaaccggga     360
gaattgatag ttgacccgaa tcctaccaag agctttgata ctgcagtata tcctgacaga     420
aagatgatag tattcctgtt tgcggaagac agcggaacag gagcgtatgc aataactaaa     480
gacggagtat ttgctacgat agtagcgaaa gtaaaagaag gagcacctaa cgggctcagt     540
gtaatcaaat ttgtagaagt aggcggattt gcgaacaatg accttgtaga acagaagaca     600
cagttctttg acggtggagt aaatgttgga gatacaacag aacctgcaac acctacaaca     660
cctgtaacaa caccgacaac aacagatgat ctagatgcag ctagcttaat taaaactagt     720
gaattctga                                                             729

<210> SEQ ID NO 25
<211> LENGTH: 448
<212> TYPE: PRT
<213> ORGANISM: Artificial Sequence
<220> FEATURE:
<223> OTHER INFORMATION: Synthetic Peptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Val Lys Leu Leu Ile
```

```
                35                  40                  45
Tyr Tyr Thr Ser Ile Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Phe Asn Lys Leu Pro Pro
                 85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Ala Ser Ile Glu Arg Leu Ser Ser Gly Leu
210                 215                 220

Arg Ile Asn Ser Ala Lys Asp Ala Ala Gly Gln Ala Ile Ala Asn
225                 230                 235                 240

Arg Phe Thr Ala Asn Ile Lys Gly Leu Thr Gln Ala Ser Arg Asn Ala
                245                 250                 255

Asn Asp Gly Ile Ser Ile Ala Gln Thr Thr Glu Gly Ala Leu Asn Glu
            260                 265                 270

Ile Asn Asn Asn Leu Gln Arg Val Arg Glu Leu Ala Val Gln Ser Ala
            275                 280                 285

Asn Ser Thr Asn Ser Gln Ser Asp Leu Asp Ser Ile Gln Ala Glu Ile
    290                 295                 300

Thr Gln Arg Leu Asn Glu Ile Asp Arg Val Ser Gly Gln Thr Gln Phe
305                 310                 315                 320

Asn Gly Val Lys Val Leu Ala Gln Asp Asn Thr Leu Thr Ile Gln Val
                325                 330                 335

Gly Ala Asn Asp Gly Glu Thr Ile Asp Ile Asp Leu Lys Gln Ile Asn
            340                 345                 350

Ser Gln Thr Leu Gly Leu Asp Ser Leu Asn Val Gln Ala Ser Gln Pro
    355                 360                 365

Glu Leu Ala Glu Ala Ala Lys Thr Thr Glu Asn Pro Leu Gln Lys
    370                 375                 380

Ile Asp Ala Ala Leu Ala Gln Val Asp Ala Leu Arg Ser Asp Leu Gly
385                 390                 395                 400

Ala Val Gln Asn Arg Phe Asn Ser Ala Ile Thr Asn Leu Gly Asn Thr
                405                 410                 415

Val Asn Asn Leu Ser Glu Ala Arg Ser Arg Ile Glu Asp Ser Asp Tyr
            420                 425                 430

Ala Thr Glu Val Ser Asn Met Ser Arg Ala Gln Ile Leu Gln Ala Ser
        435                 440                 445
```

<210> SEQ ID NO 26

<211> LENGTH: 1407
<212> TYPE: DNA
<213> ORGANISM: Artificial Sequence
<220> FEATURE:
<223> OTHER INFORMATION: Synthetic Primer

<400> SEQUENCE: 26

```
atgagggtcc ccgctcagct cctggggctc ctgctgctct ggctcccagg cgcgcgatgt      60
gatatccaga tgacacagag cccttcctcc ctgtctgcct ctgtgggaga cagagtcacc     120
atcacctgca gtgcaagtca gggcattagc aattatttaa actggtatca gcagaaacca     180
ggcaaggccg ttaaactcct gatctattac acatcaattt acactcagg agtcccatca      240
aggttcagtg gcagtgggtc tgggacagat tataccctca ccatcagctc cctgcagcct     300
gaagatttcg ccacttacta ttgtcagcag tttaataagc ttcctccgac gttcggtgga     360
ggcaccaaac tcgagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctatgcct gcgaagtcac ccatcagggc     660
ctgagctcgc ccgtcacaaa gagcttcaac aggggagagt gtgctagtat cgagcgtctg     720
tcttctggtc tgcgtatcaa cagcgcgaaa gacgatgcgg caggtcaggc gattgctaac     780
cgttttaccg cgaacatcaa aggtctgact caggcttccc gtaacgctaa cgacggtatc     840
tccatcgcgc agaccactga aggcgcgctg aacgaaatca caacaacct gcagcgtgtg      900
cgtgaactgg cggttcagtc tgctaacagc actaactccc agtctgacct cgactccatc     960
caggctgaaa tcacccagcg cctgaacgaa atcgaccgtg tatccggtca gactcagttc    1020
aacggcgtga agtcctggc gcaggacaac accctgacca tccaggttgg tgccaacgac    1080
ggtgaaacta tcgatatcga tctgaagcag atcaactctc agaccctggg cctggattca    1140
ctgaacgtgc aggctagtca accagagctg gcggaagcag ccgctaaaac caccgaaaac    1200
ccgctgcaga aaattgatgc cgcgctggcg caggtggatg cgctgcgctc tgatctgggt    1260
gcggtacaaa accgtttcaa ctccgctatc accaacttgg gcaataccgt aaacaacctg    1320
tctgaagcgc gtagccgtat cgaagattcc gactacgcga ccgaagtttc caacatgtct    1380
cgcgcgcaga ttctgcaggc tagctga                                       1407
```

<210> SEQ ID NO 27
<211> LENGTH: 658
<212> TYPE: PRT
<213> ORGANISM: Artificial Sequence
<220> FEATURE:
<223> OTHER INFORMATION: Synthetic Peptide

<400> SEQUENCE: 27

```
Gln Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Asp Ile Tyr Pro Gly Ser Gly Tyr Ser Phe Tyr Asn Glu Asn Phe
    50                  55                  60

Lys Gly Lys Ala Thr Leu Thr Ala Asp Lys Ser Ser Thr Thr Ala Tyr
```

-continued

```
             65                  70                  75                  80
        Met Gln Leu Ser Ser Leu Thr Ser Glu Asp Ser Ala Val Tyr Phe Cys
                         85                  90                  95

Ala Thr Tyr Tyr Asn Tyr Pro Phe Ala Tyr Trp Gly Gln Gly Thr Leu
                        100                 105                 110

Val Thr Val Ser Ala Ala Lys Thr Thr Gly Pro Ser Val Phe Pro Leu
                        115                 120                 125

Ala Pro Cys Ser Arg Ser Thr Ser Glu Ser Thr Ala Ala Leu Gly Cys
                        130                 135                 140

Leu Val Lys Asp Tyr Phe Pro Glu Pro Val Thr Val Ser Trp Asn Ser
        145                 150                 155                 160

Gly Ala Leu Thr Ser Gly Val His Thr Phe Pro Ala Val Leu Gln Ser
                        165                 170                 175

Ser Gly Leu Tyr Ser Leu Ser Ser Val Val Thr Val Pro Ser Ser Ser
                        180                 185                 190

Leu Gly Thr Lys Thr Tyr Thr Cys Asn Val Asp His Lys Pro Ser Asn
                        195                 200                 205

Thr Lys Val Asp Lys Arg Val Glu Ser Lys Tyr Gly Pro Pro Cys Pro
                        210                 215                 220

Pro Cys Pro Ala Pro Glu Phe Glu Gly Gly Pro Ser Val Phe Leu Phe
        225                 230                 235                 240

Pro Pro Lys Pro Lys Asp Thr Leu Met Ile Ser Arg Thr Pro Glu Val
                        245                 250                 255

Thr Cys Val Val Val Asp Val Ser Gln Glu Asp Pro Glu Val Gln Phe
                        260                 265                 270

Asn Trp Tyr Val Asp Gly Val Glu Val His Asn Ala Lys Thr Lys Pro
                        275                 280                 285

Arg Glu Glu Gln Phe Asn Ser Thr Tyr Arg Val Val Ser Val Leu Thr
                        290                 295                 300

Val Leu His Gln Asp Trp Leu Asn Gly Lys Glu Tyr Lys Cys Lys Val
        305                 310                 315                 320

Ser Asn Lys Gly Leu Pro Ser Ser Ile Glu Lys Thr Ile Ser Lys Ala
                        325                 330                 335

Lys Gly Gln Pro Arg Glu Pro Gln Val Tyr Thr Leu Pro Pro Ser Gln
                        340                 345                 350

Glu Glu Met Thr Lys Asn Gln Val Ser Leu Thr Cys Leu Val Lys Gly
                        355                 360                 365

Phe Tyr Pro Ser Asp Ile Ala Val Glu Trp Glu Ser Asn Gly Gln Pro
                        370                 375                 380

Glu Asn Asn Tyr Lys Thr Thr Pro Pro Val Leu Asp Ser Asp Gly Ser
        385                 390                 395                 400

Phe Phe Leu Tyr Ser Arg Leu Thr Val Asp Lys Ser Arg Trp Gln Glu
                        405                 410                 415

Gly Asn Val Phe Ser Cys Ser Val Met His Glu Ala Leu His Asn His
                        420                 425                 430

Tyr Thr Gln Lys Ser Leu Ser Leu Ser Leu Gly Lys Ala Ser Met His
                        435                 440                 445

Gly Pro Lys Ala Thr Leu Gln Asp Ile Val Leu His Leu Glu Pro Gln
                        450                 455                 460

Asn Glu Ile Pro Val Asp Leu Leu Gly His Gly Gln Leu Ser Asp Ser
        465                 470                 475                 480

Glu Glu Glu Asn Asp Glu Ile Asp Gly Val Asn His Gln His Leu Pro
                        485                 490                 495
```

-continued

```
Ala Arg Arg Ala Glu Pro Gln Arg His Thr Met Leu Cys Met Cys Cys
            500                 505                 510

Lys Ala Ser Met Ala Arg Phe Glu Asp Pro Thr Arg Pro Tyr Lys
        515                 520                 525

Leu Pro Asp Leu Cys Thr Glu Leu Asn Thr Ser Leu Gln Asp Ile Glu
    530                 535                 540

Ile Thr Cys Val Tyr Cys Lys Thr Val Leu Glu Leu Thr Glu Val Gly
545                 550                 555                 560

Glu Phe Ala Phe Lys Asp Leu Phe Val Val Tyr Arg Asp Ser Ile Pro
                565                 570                 575

His Ala Ala Cys His Lys Cys Ile Asp Phe Tyr Ser Arg Ile Arg Glu
            580                 585                 590

Leu Arg His Tyr Ser Asp Ser Val Tyr Gly Asp Thr Leu Glu Lys Leu
        595                 600                 605

Thr Asn Thr Gly Leu Tyr Asn Leu Leu Ile Arg Cys Leu Arg Cys Gln
    610                 615                 620

Lys Pro Leu Asn Pro Ala Ser Ser Val Ser Pro Thr Thr Ser Val
625                 630                 635                 640

His Pro Thr Pro Thr Ser Val Pro Pro Thr Pro Thr Lys Ser Ser Pro
                645                 650                 655

Ala Ser

<210> SEQ ID NO 28
<211> LENGTH: 2031
<212> TYPE: DNA
<213> ORGANISM: Artificial Sequence
<220> FEATURE:
<223> OTHER INFORMATION: Synthetic Primer

<400> SEQUENCE: 28
atggaatgga ggatctttct cttcatcctg tcaggaactg caggtgtcca ctcccaggtt      60
cagctgcggc agtctggacc tgagctggtg aagcctgggg cttcagtgaa gatgtcctgc     120
aaggcttctg gatacacatt tactgactat gttataagtt gggtgaagca gagaactgga     180
cagggccttg agtggattgg agatatttat cctggaagtg gttattcttt ctacaatgag     240
aacttcaagg gcaaggccac actgactgca gacaaatcct ccaccacagc ctacatgcag     300
ctcagcagcc tgacatctga ggactctgcg gtctatttct gtgcaaccta ctataactac     360
ccttttgctt actggggcca agggactctg gtcactgtct ctgcagccaa acaacgggc     420 ccatccgtct tccccctggc gccctgctcc aggagcacct ccgagagcac agccgccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcacga agacctacac ctgcaacgta     660
gatcacaagc ccagcaacac caaggtggac aagagagttg agtccaaata tggtccccca     720
tgcccaccct gcccagcacc tgagttcgaa ggggaccat cagtcttcct gttcccccca     780
aaacccaagg acactctcat gatctcccgg acccctgagg tcacgtgcgt ggtggtggac     840
gtgagccagg aagaccccga ggtccagttc aactggtacg tggatggcgt ggaggtgcat     900
aatgccaaga caaagccgcg ggaggagcag ttcaacagca cgtaccgtgt ggtcagcgtc     960
ctcaccgtcc tgcaccagga ctggctgaac ggcaaggagt acaagtgcaa ggtctccaac    1020
aaaggcctcc cgtcctccat cgagaaaacc atctccaaag ccaaagggca gccccgagag    1080
```

-continued

```
ccacaggtgt acaccctgcc cccatcccag gaggagatga ccaagaacca ggtcagcctg    1140
acctgcctgg tcaaaggctt ctaccccagc gacatcgccg tggagtggga gagcaatggg    1200
cagccggaga caactacaa gaccacgcct cccgtgctgg actccgacgg ctccttcttc     1260
ctctacagca ggctaaccgt ggacaagagc aggtggcagg aggggaatgt cttctcatgc    1320
tccgtgatgc atgaggctct gcacaaccac tacacacaga gagcctctc cctgtctctg     1380 ggtaaagcta gtatgcacgg gcctaaggcc acactgcaag atattgtcct ccatctcgaa    1440
ccccagaatg agataccagt ggaccttctg ggccacggac agttgtccga tagcgaggag    1500
gaaaacgacg aaatcgacgg tgttaaccac cagcacttgc cggctcggag ggcagagccc    1560
cagagacata ccatgctgtg catgtgttgc aaagctagta tggccagatt cgaggatcca    1620
acacgccgac cttacaaatt gccggacctt gcacggagc tgaacacttc cctgcaggac     1680
atagaaatta cctgcgtcta ctgcaagacc gttctcgaac tgacagaagt aggcgagttt    1740
gcgtttaaag atctgttcgt ggtgtatcgg gatagcattc cccacgcagc ttgtcataag    1800
tgtatcgact ctattctag gatccgggag ctcagacact atagcgattc cgtgtacggc     1860
gacacacttg agaagctcac taacaccggg ctgtacaacc tcctgatccg gtgcttgagg    1920
tgtcagaaac ccctgaatcc tgctagtagc agcgtgagcc ccaccaccag cgtgcacccc    1980 accccccacca gcgtgccccc cacccccacc aagagcagcc ccgctagctg a            2031
```

<210> SEQ ID NO 29
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 29

Pro Thr Ser Thr Pro Ala Asp Ser Ser Thr Ile Thr Pro Thr Ala Thr
1               5                   10                  15

Pro Thr Ala Thr Pro Thr Ile Lys Gly
            20                  25

<210> SEQ ID NO 30
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 30

Thr Val Thr Pro Thr Ala Thr Ala Thr Pro Ser Ala Ile Val Thr Thr
1               5                   10                  15

Ile Thr Pro Thr Ala Thr Thr Lys Pro
            20                  25

<210> SEQ ID NO 31
<211> LENGTH: 25
<212> TYPE: PRT
<213> ORGANISM: Artificial Sequence
<220> FEATURE:
<223> OTHER INFORMATION: Synthetic Peptide

```
<400> SEQUENCE: 31

Thr Asn Gly Ser Ile Thr Val Ala Ala Thr Ala Pro Thr Val Thr Pro
1               5                   10                  15

Thr Val Asn Ala Thr Pro Ser Ala Ala
            20              25
```

VACCINES AGAINST HPV AND HPV-RELATED DISEASES

This application is a continuation of U.S. patent application Ser. No. 16/397,214, filed Apr. 29, 2019, which is a continuation of U.S. patent application Ser. No. 15/111,357, filed Jul. 13, 2016, now issued U.S. Pat. No. 10,286,058, issued May 14, 2019, which is a national phase application under 35 U.S.C. § 371 of International Application No. PCT/US2015/011236, filed Jan. 13, 2015, which claims the benefit of priority to U.S. Provisional Patent Application Ser. No. 61/926,821, filed Jan. 13, 2014, and U.S. Provisional Patent Application Ser. No. 62/002,718, filed May 23, 2014, the entire contents of each of which are hereby incorporated by reference in their entirety.

The invention was made with government support under Grant No. U19 AI057234 awarded by the National Institutes of Health and the National Institute of Allergy and Infectious Diseases. The government has certain rights in the invention.

BACKGROUND OF THE INVENTION

1. Field of the Invention

The present invention relates generally to the field of medicine. More particularly, it concerns new and novel vaccines against Human Papilloma Virus (HPV) and HPV-related diseases, including multiple types of cancers.

2. Description of Related Art

Human papillomavirus (HPV) is one of the most common sexually-transmitted pathogens. Current HPV prophylactic vaccine have shown significant clinical efficacy in the prevention of HPV infection, but it exhibits no efficacy in the treatment of infected patients and HPV-related cancers. HPV infection causes virtually all cervical cancers, and many anal, vaginal, vulvar, penile, and oropharyngeal (throat) cancers. Thus, the development of safe and effective vaccines for patients who are infected with HPV and have HPV-related cancers are in high demand. HPV infection also causes HIV-related malignancy and cancers.

Current HPV vaccines are recombinant virus-like particles made of capsid (L1) proteins of HPV 6, 11, 16, and 18. These vaccines can elicit strong antibody responses and thus can prevent HPV infection. To suppress viral replication and to eradicate HPV-related cancers, vaccines need to evoke strong T cell responses, particularly cytotoxic CD8+ lymphocytes (CTLs) that can kill virus-infected cells followed by the inhibition of HPV replication as well as HPV-related tumor cells.

Several types of vaccine models (including peptides, proteins, and DNA-based vaccines and vaccines carried by live-attenuated vectors) have been tested, but these vaccines have drawbacks either in efficacy or safety particularly in immunodeficient patients. This gap necessitates developing safe and potent immunotherapeutic vaccines against HPV-associated cancer.

A wealth of evidence has led to the conclusion that virtually all cases of cervical cancer are attributable to persistent infection by a subset of HPV types, especially HPV type 16 (HPV 16) and HPV type 18 (HPV 18). These HPV types also cause a proportion of other cancers of mucosa, including vulvar, vaginal, anal, penile, and oropharyngeal cancers. HPV 16 is the predominant type in squamous cell carcinoma of the cervix, and HPV 18 is the second most common type with prevalence ranging from 12.6% in Central/South America to 25.7% in South Asia. In addition, HPV 18 has been implicated in rapidly developing and potentially more aggressive cervical carcinomas. However, subclinical infections are the most common manifestation of HPV infection. Different studies reported between 15% and 36% of subclinical infections in sexually active adults.

SUMMARY OF THE INVENTION

Disclosed is a fusion protein comprising an anti-CD40 antibody or fragment thereof, comprising at least three complementarity determining regions from an anti-CD40 antibody, at least one peptide linker, and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises at least the variable region from an anti-CD40 antibody. The variable region can be from a light chain or heavy chain. In some embodiments, the anti-CD40 antibody or fragment thereof comprises at least the variable region from an anti-CD40 antibody light chain and at least the variable region from an anti-CD40 antibody heavy chain. In some embodiments, the anti-CD40 antibody or fragment thereof comprises six CDRs from an anti-CD40 antibody. In some embodiments, the anti-CD40 antibody or fragment thereof is humanized. In some embodiments, the peptide linker or linkers are a flexible linker. In some embodiments, the peptide linker or linkers comprise one or more glycosylation sites. In some embodiments, the peptide linker or linkers are Flexv1 (SEQ ID NO:5) and/or f1 (SEQ ID NO:6). In some embodiments, the HPV antigens are E6 and E7. In some embodiments, the fusion protein comprises the sequence of SEQ ID NO:19. In some embodiments, the fusion protein comprises the sequence of SEQ ID NO:21. In some embodiments, at least one HPV E6 antigen is an HPV type 16 antigen and at least one HPV E6 antigen is an HPV type 18 antigen. In some embodiments, at least one HPV E7 antigen is an HPV type 16 antigen and at least one HPV E7 antigen is an HPV type 18 antigen. In some embodiments, at least one HPV E6 antigen is an HPV type 16 antigen and at least one HPV E6 antigen is an HPV type 18 antigen and at least one HPV E7 antigen is an HPV type 16 antigen and at least one HPV E7 antigen is an HPV type 18 antigen.

Also disclosed is a fusion protein comprising the amino acid sequences of at least SEQ ID NOs:11-13 or SEQ ID NOs:14-16 and at least one human papillomavirus (HPV) E6 or E7 antigen. In some embodiments, the fusion protein comprises SEQ ID NOs:11-13 and SEQ ID NOs:14-16. In some embodiments, the E6 or E7 antigen or antigens are HPV type 16 or HPV type 18 antigens. In some embodiments, the fusion protein further comprises a peptide linker. In some embodiments, the peptide linker is a flexible linker. In some embodiments, the peptide linker comprises one or more glycosylation sites. In some embodiments, the peptide linker is Flexv1 (SEQ ID NO:5) and/or f1 (SEQ ID NO:6).

Also disclosed is a pharmaceutical composition comprising any of the above fusion proteins.

Also disclosed is a method of making any of the above fusion proteins comprising isolating the fusion protein from a recombinant host cell expressing the fusion protein.

Also disclosed is a composition comprising a dendritic cell targeting complex comprising an anti-CD40 antibody or fragment thereof comprising at least three complementarity determining regions from an anti-CD40 antibody, at least one peptide linker and at least one human papillomavirus (HPV) E6 or E7 antigen, wherein the E6 or E7 antigen or antigens are an HPV type 16 or HPV type 18 antigen. In some embodiments, the anti-CD40 antibody or fragment thereof comprises at least the variable region from an anti-CD40 antibody. The variable region can be from a light chain or heavy chain. In some embodiments, the anti-CD40 antibody or fragment thereof comprises at least the variable region from an anti-CD40 antibody light chain and at least the variable region from an anti-CD40 antibody heavy chain. In some embodiments, the anti-CD40 antibody or fragment thereof comprises six CDRs from an anti-CD40 antibody. In some embodiments, the anti-CD40 antibody or fragment thereof is humanized. In some embodiments, the peptide linker or linkers are a flexible linker. In some embodiments, the peptide linker or linkers comprise one or more glycosylation sites. In some embodiments, the peptide linker or linkers are selected from Flexv1 (SEQ ID NO:5) or f1 (SEQ ID NO:6). In some embodiments, the HPV antigens are E6 and E7. In some embodiments, the fusion protein comprises the sequence of SEQ ID NO:19. In some embodiments, the fusion protein comprises the sequence of SEQ ID NO:21. In some embodiments, at least one HPV E6 antigen is an HPV type 16 antigen and at least one HPV E6 antigen is an HPV type 18 antigen. In some embodiments, at least one HPV E7 antigen is an HPV type 16 antigen and at least one HPV E7 antigen is an HPV type 18 antigen. In some embodiments, at least one HPV E6 antigen is an HPV type 16 antigen and at least one HPV E6 antigen is an HPV type 18 antigen and at least one HPV E7 antigen is an HPV type 16 antigen and at least one HPV E7 antigen is an HPV type 18 antigen.

In some embodiments the HPV E6 and E7 antigens are selected from SEQ ID NO: 1-4. In other embodiments the HPV E6 and E7 antigens are at least 70%, 75%, 80%, 85%, 90%, 95%, 98%, 99% or 100%, or any range derivable therein, identical to any combination of SEQ ID NO: 1-4. In other embodiments the HPV E6 and E7 antigens are at least 70%, 75%, 80%, 85%, 90%, 95%, 98%, 99% or 100%, or any range derivable therein, identical to SEQ ID NO: 1-4. In still other embodiments, the HPV E6 antigen is a 50, 55, 60, 65, 70, 75, 80, 85, 90, 95, 100, 105, 110, 115 or 120, or any range derivable therein, subset of contiguous amino acids of SEQ ID NO: 1 and/or 3 and the HPV E7 antigen is a 50, 55, 60, 65, 70, 75, 80, 85, 90, 95, 100, 105, 110, 115 or 120, or any range derivable therein, subset of contiguous amino acids of SEQ ID NO: 2 and/or 4.

Also disclosed is a vector comprising a polynucleotide sequence encoding a fusion protein comprising an anti-CD40 antibody or fragment thereof comprising at least three complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region. In some embodiments, the anti-CD40 antibody or fragment thereof comprises an anti-CD40 antibody heavy chain variable region. In some embodiments, the polynucleotide sequence encodes at least one HPV type 16 E6 antigen, at least one HPV type 16 E7 antigen or at least one HPV type 18 E6 antigen and at least one HPV type 18 E7 antigen. In some embodiments, the polynucleotide sequence encodes a polypeptide comprising SEQ ID NO: 19. In some embodiments, the polynucleotide sequence encodes a polypeptide comprising SEQ ID NO: 21. In some embodiments, the polynucleotide sequence encodes at least one HPV type 16 E6 antigen, at least one HPV type 16 E7 antigen, at least one HPV type 18 E6 antigen and at least one HPV type 18 E7 antigen.

Also disclosed is a method for preventing a human papillomavirus (HPV) infection comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, dendritic cell targeting complex comprises SEQ ID NO: 21. In some embodiments, the composition further comprises an adjuvant. In some embodiments, the method further comprises administering to the patient a separate HPV vaccine. In some embodiments, the separate HPV vaccine is Gardasil™ or Cervarix™.

Also disclosed is a method for treating a human papillomavirus (HPV) infection comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the method further comprises administering to the patient a separate HPV treatment.

Also disclosed is a method for inducing an immune response to at least one HPV epitope comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the composition further comprises an adjuvant. In some embodiments, the method further comprises administering to the patient a separate HPV vaccine. In some embodiments, the separate HPV vaccine is Gardasil™ or Cervarix™.

Also disclosed is a method for potentiating an immune response to at least one HPV epitope comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, potentiating an immune response is directed towards potentiating or increasing or enhancing memory T-cells. In some embodiments, the method further comprises administering to the patient a separate HPV treatment.

Also disclosed is a method for preventing a human papillomavirus (HPV) related disease comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the composition further comprises an adjuvant. In some embodiments, the HPV related disease is dysplasia, benign neoplasia, pre-malignant neoplasia or cancer. In some embodiments, the HPV related disease is cancer. In some embodiments, the cancer is cancer of the cervix, vulva, vagina, penis, anus, oropharynx, throat or lung. In some embodiments, the method further comprises administering to the patient a separate HPV vaccine. In some embodiments, the separate HPV vaccine is Gardasil™ or Cervarix™.

Also disclosed is a method for treating a human papillomavirus (HPV) related disease comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the HPV related disease is dysplasia, benign neoplasia, pre-malignant neoplasia or cancer. In some embodiments, the HPV related disease is cancer. In some embodiments, the cancer is cancer of the cervix, vulva, vagina, penis, anus, oropharynx, throat or lung. In yet further embodiments, the cancer is head and neck cancer. In some embodiments, the method further comprises administering to the patient a separate treatment. In some embodiments, the method further comprises administering to the patient a cancer treatment.

Also disclosed is a method of inhibiting HPV-infected cells in a patient comprising administering to the patient an effective amount of a composition comprising any of the above fusion proteins or vectors. In some embodiments, the HPV-infected cells are in a tumor.

Also disclosed is a method of reducing the size or mass of a tumor in a patient that is suffering from an HPV infection or the tumor comprises HPV-infected cells, comprising administering to the patient an effective amount of a composition comprising any of the above fusion proteins or vectors. The percent reduction in size or mass of the tumor or the percent regression of the tumor during or following treatment may be at least 10%, 20%, 25%, 30%, 35%, 40%, 45%, 50%, 55%, 60%, 65%, 70% 75%, 80%, 85%, 90%, 95% to 100% or any derivable range therein. The percent reduction in size or mass of the tumor or the percent regression of the tumor may be such that the tumor size eases discomfort and improves the patient's quality of life or leads to, or is associated with, a clinically favorable outcome.

Disclosed is a method of extending survival or a patient or subject suffering from an HPV related disease comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the HPV related disease is dysplasia, benign neoplasia, pre-malignant neoplasia or cancer. In some embodiments, the HPV related disease is cancer. In some embodiments, the cancer is cancer of the cervix, vulva, vagina, penis, anus, oropharynx, throat or lung. In yet further embodiments, the cancer is head and neck cancer. In some embodiments, the method further comprises administering to the patient a separate treatment. In some embodiments, the method further comprises administering to the patient a cancer treatment. In some aspects, survival is extended by a period of 1, 2, 3, 4, 5, 6, 7, 8, 9 or 10 days, or any range derivable therein. In some aspects, survival is extended by a period of 1, 2, 3, 4, 5, 6, 7, 8, 9 or 10 weeks, or any range derivable therein. In some aspects, survival is extended by a period of 1, 2, 3, 4, 5, 6, 7, 8, 9 or 10 months, or any range derivable therein. In some aspects, survival is extended by a period of 1, 2, 3, 4, 5, 6, 7, 8, 9, 10, 11, 12, 13, 14, 15, 20, 25 or 30 years, or any range derivable therein.

Any of the methods disclosed above may be implemented using any of the fusion proteins, compositions, and/or vectors disclosed above.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
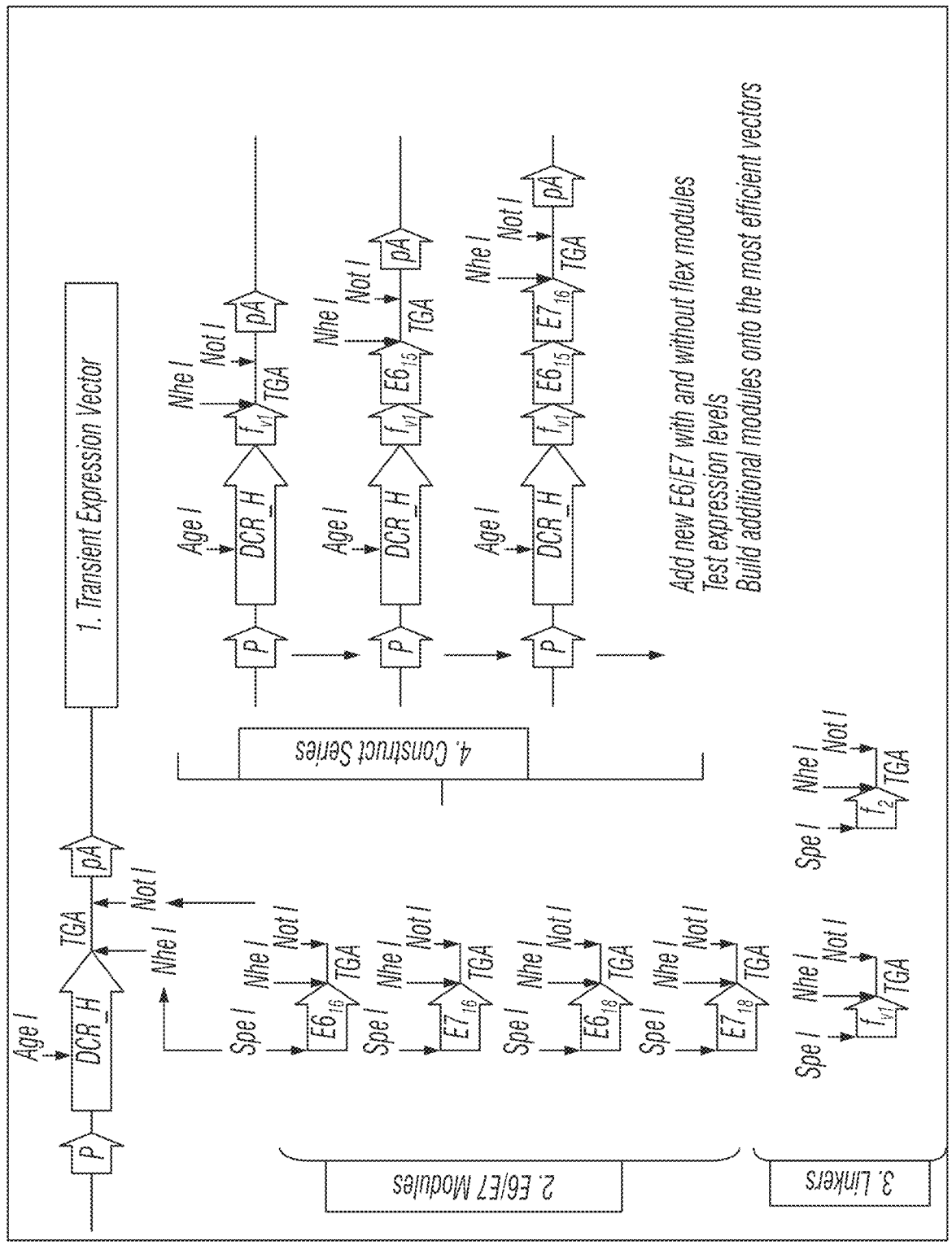
FIG. 1: Scheme for development of recombinant anti-DC receptor-E6/E7 vaccines.
Figure 2:
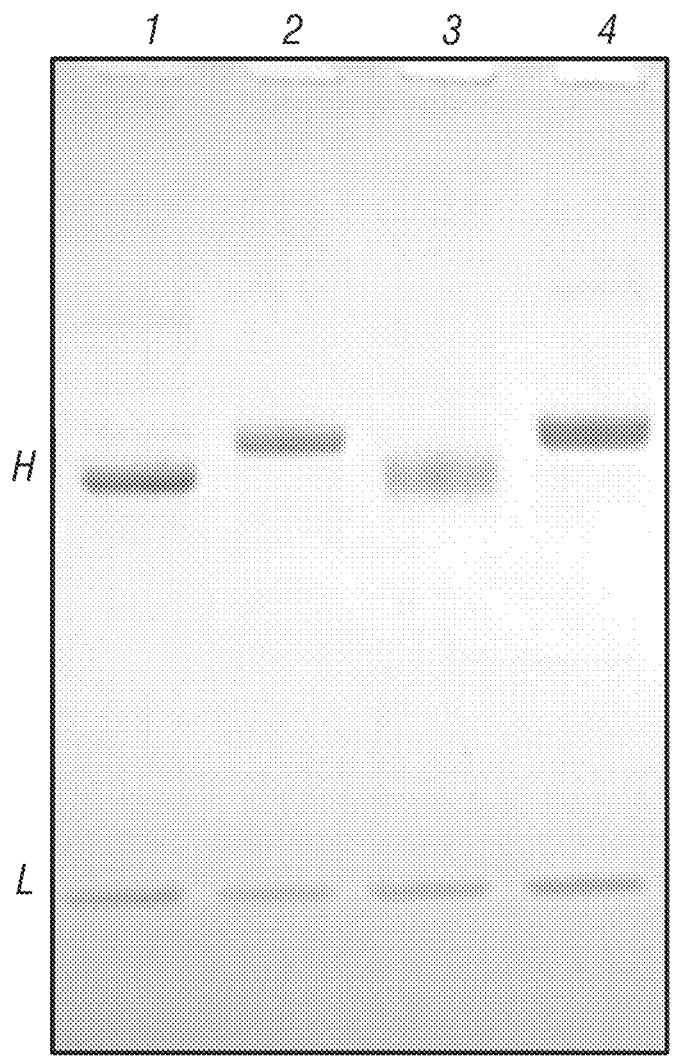
FIG. 2: SDS-PAGE analysis of protein A affinity purified anti-DC receptor antibody fused to HPV16 E6 and E7 antigens.
Figure 3:
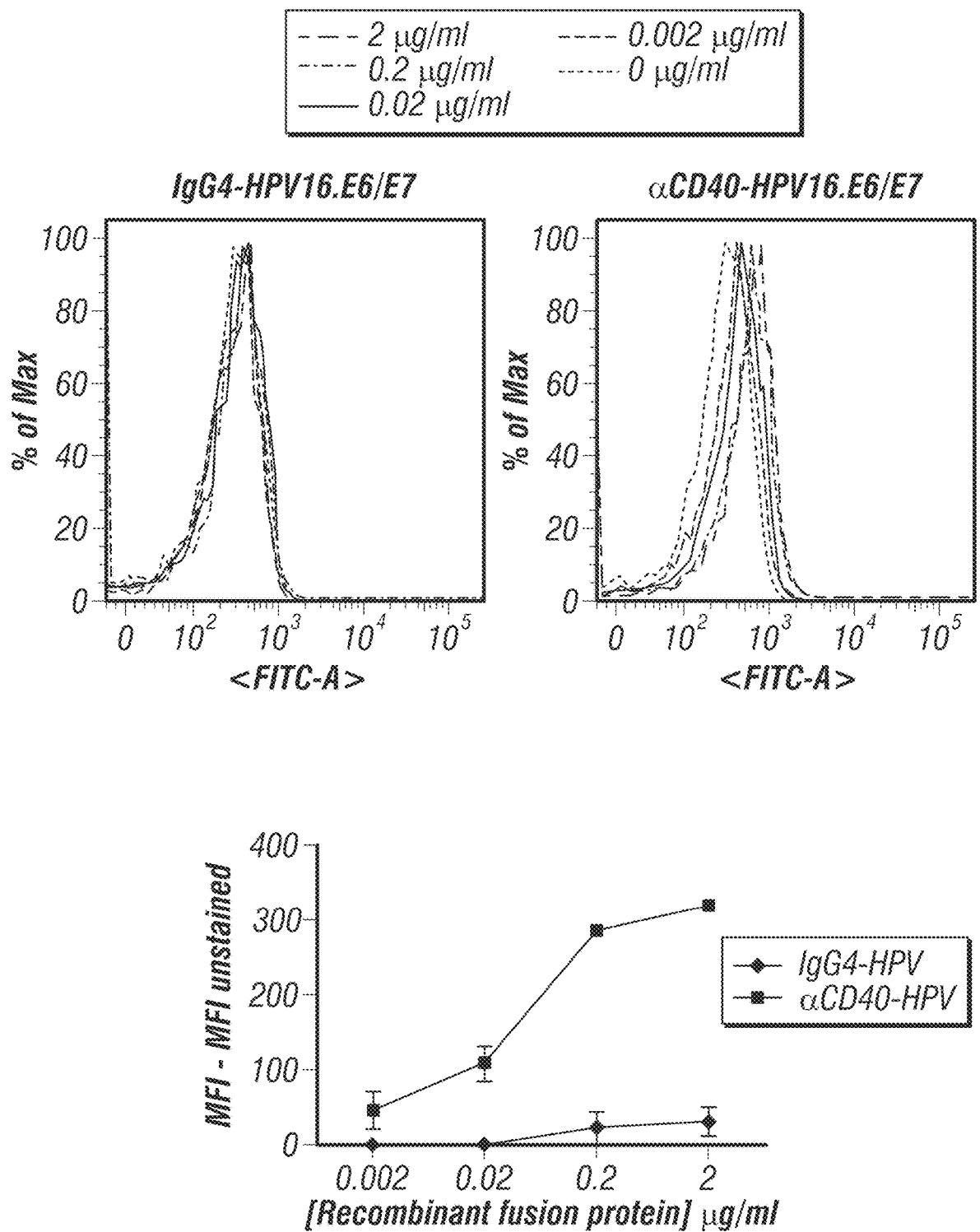
FIG. 3: Anti-CD40-HPV16.E6/7 can efficiently bind to human blood DCs.

As described in the Examples, an anti-CD40 antibody to which an HPV E6 and E7 antigen has been fused (called hereafter 'anti-CD40-HPV16.E6/7') has been shown to induce a strong immune response against said antigens (including a strong T-cell response). This provides an efficient and effective method of eliciting and potentiating an immune response to HPV antigens. Moreover, an anti-CD40-HPV16.E6/7 has been used in a prime-boost strategy in combination with a poly IC adjuvant to suppress TC-1 tumor progression in human CD40 transgenic mice. Thus, it has been demonstrated that said anti-CD40-HPV16.E6/7 can elicit E6/E7-specific CD8+ cytotoxic T lymphocytes and when administered with a poly IC adjuvant, serves as an efficient vaccine.

I. NUCLEIC ACIDS

In certain embodiments, there are recombinant nucleic acids encoding the proteins, polypeptides, or peptides described herein. Polynucleotides contemplated for use in methods and compositions include those encoding antibodies to DC receptors or binding portions thereof, HPV antigens, linker regions or adjuvants.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or fewer in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode polypeptides (e.g., an antibody or fragment thereof) that bind to DC receptors, are HPV antigens, are linker regions or are fusion proteins comprising any combination of a DC receptor antibody or antibodies or fragments thereof, HPV antigens (such as E6 or E7 from any HPV type) and linker regions. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody or fragment thereof that binds a dendritic cell receptor, an HPV antigen or antigens (e.g. E6 and/or E7 from one or multiple HPV types), a linker or multiple linker regions, an adjuvant or multiple adjuvants, any combination of the aforementioned proteins or a fusion protein or fusion proteins comprising any combination of the aforementioned proteins.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

II. PROTEINACEOUS COMPOSITIONS

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table, below).

| Codon Table | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules or loss of antigenicity in antigenic peptides or proteins. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total polypeptide, peptide, and/or protein per ml. Thus, the concentration of protein (including a fusion protein) in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an antibody that binds DC receptor or a fusion protein comprising an antibody that binds a DC receptor, and may be used in combination with other HPV antigens, linker regions or adjuvants described herein.

Polypeptides and Polypeptide Production

Embodiments involve polypeptides, peptides, and proteins and immunogenic fragments thereof for use in various aspects described herein. For example, specific antibodies are assayed for or used in binding to DC receptors and presenting HPV antigens. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects an DC receptor or receptor fragment comprises substantially all of the extracellular domain of a protein which has at least 85% identity, at least 90% identity, at least 95% identity, or at least 97-99% identity, including all values and ranges there between, to a sequence selected over the length of the fragment sequence.

Also included in immunogenic compositions are fusion proteins composed of HPV antigens, or immunogenic fragments of HPV antigens (e.g., E6 or E7). HPV antigens may be from any type (e.g. type 16 or type 18). For example an HPV antigen may be selected from a single or combination of HPV type. An HPV antigen or combination of HPV antigen may be from HPV type 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120. Alternatively, embodiments also include individual fusion proteins of HPV proteins or immunogenic fragments thereof or anti-DC receptor antibodies or fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

Antibodies and Antibody-Like Molecules

In certain aspects, one or more antibodies or antibody-like molecules (e.g., polypeptides comprising antibody CDR domains) may be obtained or produced which have a specificity for a DC receptor. These antibodies may be used in various diagnostic or therapeutic applications described herein.

As used herein, the term "antibody" is intended to refer broadly to any immunologic binding agent such as IgG, IgM, IgA, IgD and IgE as well as polypeptides comprising antibody CDR domains that retain antigen binding activity. Thus, the term "antibody" is used to refer to any antibody-like molecule that has an antigen binding region, and includes antibody fragments such as Fab', Fab, F(ab')2, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region (Pack, et al., 1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al., 2003 describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate DC receptor-binding molecules in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra, 2001), protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as DC receptor-binding molecules. Such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibiters of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin. In order to describe antibodies of some embodiments, the strength with which an antibody molecule binds an epitope, known as affinity, can be measured. The affinity of an antibody may be determined by measuring an association constant (Ka) or dissociation constant (Kd). Antibodies deemed useful in certain embodiments may have an association constant of about, at least about, or at most about 10e6, 10e7, 10e8, 10e9 or 10e10 M or any range derivable therein. Similarly, in some embodiments antibodies may have a dissociation constant of about, at least about or at most about 10e-6, 10e-7, 10e-8, 10e-9 or 10e-10. M or any range derivable therein. These values are reported for antibodies discussed herein and the same assay may be used to evaluate the binding properties of such antibodies In certain embodiments, a polypeptide that specifically binds to DC receptors is able to bind a DC receptor on the surface of the cells and present an HPV antigen that allows the generation of a robust immune response. Moreover, in some embodiments, the polypeptide that is used can provided protective immunity against HPV or provides a means of therapy for HPV by generating a robust immune response.

1. Methods for Generating Antibodies

Methods for generating antibodies (e.g., monoclonal antibodies and/or monoclonal antibodies) are known in the art. Briefly, a polyclonal antibody is prepared by immunizing an animal with a DC receptor polypeptide or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include any acceptable immunostimulatory compound, such as cytokines, chemokines, cofactors, toxins, plasmodia, synthetic compositions or vectors encoding such adjuvants.

Adjuvants that may be used in accordance with embodiments include, but are not limited to, IL-1, IL-2, IL-4, IL-7, IL-12, -interferon, GMCSP, BCG, aluminum hydroxide, MDP compounds, such as thur-MDP and nor-MDP, CGP (MTP-PE), lipid A, poly IC, montaninde, GMCSF, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, N.J.), cytokines such as -interferon, IL-2, or IL-12 or genes encoding proteins involved in immune helper functions, such as B-7.

The amount of immunogen composition used in the production of antibodies varies upon the nature of the immunogen as well as the animal used for immunization. A variety of routes can be used to administer the immunogen including but not limited to subcutaneous, intramuscular, intradermal, intraepidermal, intravenous, intratumoral and intraperitoneal. The production of antibodies may be monitored by sampling blood of the immunized animal at various points following immunization.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. In some embodiments, Rodents such as mice and rats are used in generating monoclonal antibodies. In some embodiments, rabbit, sheep or frog cells are used in generating monoclonal antibodies. The use of rats is well known and may provide certain advantages (Goding, 1986, pp. 60 61). Mice (e.g., BALB/c mice) are routinely used and generally give a high percentage of stable fusions.

MAbs produced by either means may be further purified, if desired, using filtration, centrifugation and various chromatographic methods such as HPLC or affinity chromatography. Fragments of the monoclonal antibodies so produced can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination which further increases the chance of finding appropriate antibodies.

Another embodiment concerns producing antibodies, for example, as is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments can be synthesized using an automated peptide synthesizer, or by expression of full-length gene or of gene fragments in *E. coli*.

It is further contemplated that monoclonal antibodies may be further screened or optimized for properties relating to specificity, avidity, half-life, immunogenicity, binding association, binding disassociation, or overall functional properties relative to the intended treatment or protective effect. Thus, it is contemplated that monoclonal antibodies may have 1, 2, 3, 4, 5, 6, or more alterations in the amino acid sequence of 1, 2, 3, 4, 5, or 6 CDRs of monoclonal antibodies or humanized antibodies provided herein. It is contemplated that the amino acid in position 1, 2, 3, 4, 5, 6, 7, 8, 9, or 10 of CDR1, CDR2, CDR3, CDR4, CDR5, or CDR6 of the VJ or VDJ region of the light or heavy variable region of antibodies may have an insertion, deletion, or substitution with a conserved or non-conserved amino acid. Such amino acids that can either be substituted or constitute the substitution are disclosed above.

In some embodiments, fragments of a whole antibody can perform the function of binding antigens. Examples of binding fragments are (i) the Fab fragment constituted with the VL, VH, CL and CH1 domains; (ii) the Fd fragment consisting of the VH and CH1 domains; (iii) the Fv fragment constituted with the VL and VH domains of a single antibody; (iv) the dAb fragment (Ward, 1989; McCafferty et al., 1990; Holt et al., 2003), which is constituted with a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988; Huston et al., 1988); (viii) bispecific single chain Fv dimers (PCT/US92/09965) and (ix) "diabodies", multivalent or multispecific fragments constructed by gene fusion (WO94/13804; Holliger et al., 1993). Fv, scFv or diabody molecules may be stabilized by the incorporation of disulphide bridges linking the VH and VL domains (Reiter et al., 1996). Minibodies comprising a scFv joined to a CH3 domain may also be made (Hu et al. 1996). The citations in this paragraph are all incorporated by reference.

Antibodies also include bispecific antibodies. Bispecific or bifunctional antibodies form a second generation of monoclonal antibodies in which two different variable regions are combined in the same molecule (Holliger & Winter, 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger et al, 1993), e.g. prepared chemically or from hybrid hybridomas, or may be any of the bispecific antibody fragments mentioned above. These antibodies can be obtained by chemical methods (Glennie et al., 1987; Repp et al., 1995) or somatic methods (Staerz & Bevan, 1986) but likewise by genetic engineering techniques which allow the heterodimerization to be forced and thus facilitate the process of purification of the antibody sought (Merchand et al., 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. The citations in this paragraph are all incorporated by reference.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against a DC receptor, then a library can be made where the other arm is varied and an antibody of appropriate specificity selected. Bispecific whole antibodies may be made by alternative engineering methods as described in Ridgeway et al., 1996), which is hereby incorporated by reference.

Antibody and Polypeptide Conjugates

Embodiments provide antibodies and antibody-like molecules against DC receptors, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity or immunostimulatory activity. Non-limiting examples of effector molecules which have been attached to antibodies include adjuvants, toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin. The following US patent applications are incorporated by reference to the extent they disclose antibodies, portions of antibodies, antigens, linkers, specific sequences of such antibodies, antigens and linkers, adjuvants, other components of a fusion protein or therapeutic composition, host cell or composition, sources of dendritic cells and culturing/activating of dendritic cells and derivatives of and from dendritic cells, and methods of use involving such fusion proteins: Ser. Nos. 12/024,036; 12/024,897; 12/025,010; 12/026,095; 12/036,138; 12/036,158; 12/504,463; 12/717,778; 12/717,789; 12/717,804; 12/718,365; 12/882,052; 12/882,052; 13/100,684; 13/208, 993; 13/269,951; 13/282,112; 13/415,564; 13/424,582; 13/430,206; 13/594,397; 13/596,526; WO2010/104749; 13/465,371; 13/397,932; PCT/US13/72217; and PCT/US2013/05839.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948 (incorporated herein by reference), imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987, incorporated herein by reference). This approach has been reported to produce diagnostically and therapeutically promising antibodies which are currently in clinical evaluation.

2. Dendritic Cell Specific Antibodies

In certain aspects, antibodies used to target HPV antigens to dendritic cells are dendritic cell specific antibodies and bind dendritic cell receptors or receptors expressed by dendritic cells. Some of the antibodies that may be used for this purpose are known in the art.

In some embodiments anti-DCIR antibodies are used to target HPV antigens to dendritic cells. One example includes anti-dendritic cell immunoreceptor monoclonal antibody conjugates, wherein the conjugate comprises antigenic peptides that are loaded or chemically coupled to the antibody. Such antibodies are described in U.S. application No. 61/332,465 and are incorporated herein by reference.

In other embodiments anti-CD40 antibodies are used to target HPV antigens to dendritic cells. Compositions and methods for the expression, secretion and use of anti-CD40 antibodies as vaccines and antigen delivery vectors with one linked antigenic peptides are described in WO 2010/104761; all methods disclosed are incorporated herein by reference. In some embodiments the anti-CD40 antibody comprises the heavy chain and light chain variable region from monoclonal antibody 12E12, 11B6 or 12B4. In other embodiments the anti-CD40 antibody comprises the heavy chain and light chain CDRs from monoclonal antibody 12E12, 11B6 or 12B4.

In certain aspects anti-LOX-1 antibodies are used to target HPV antigens to dendritic cells. One example of such an antibody can be used to target the LOX-1 receptor on immune cells and increase the effectiveness of antigen presentation by LOX-1 expressing antigen presenting cells. Examples of such LOX-1 antibodies are described in WO 2008/103953, the contents of which are incorporated herein by reference.

In other aspects anti-CLEC-6 antibodies are used to target HPV antigens to dendritic cells. One example of such antibodies include anti-CLEC-6 antibodies used to increase the effectiveness of antigen presentation by CLEC-6 expressing antigen presenting cells. Such antibodies are described in WO 2008/103947, the methods and contents of which are incorporated herein by reference.

In yet other embodiments anti-Dectin-1 antibodies are used to target HPV antigens to dendritic cells. Anti-Dectin-1 antibodies that increase the effectiveness of antigen presentation by Dectin-1 expressing antigen presenting cells are described in WO 2008/118587, the contents of which are incorporated herein by reference.

In certain aspects, peptide linkers are used to link dendritic cell specific antibodies and HPV antigens to be presented. Peptide linkers may incorporate glycosylation sites or introduce secondary structure. Additionally these linkers increase the efficiency of expression or stability of the fusion protein and as a result the efficiency of antigen presentation to a dendritic cell. Such linkers may include SSVSPTTSVHPTPTSVPPTPTKSSP (SEQ ID NO: 6); PTSTPADSSTITPTATPTATPTIKG (SEQ ID NO:29); TVTPTATATPSAIVTTITPTATTKP (SEQ ID NO:30); QTPTNTISVTPTNNSTPTNNSNPKPNP (SEQ ID NO: 5); or TNGSITVAATAPTVTPTVNATPSAA (SEQ ID NO: 31). These examples and others are discussed in WO 2010/104747, the contents of which are incorporated herein by reference.

In other embodiments an immune adjuvant is directly fused to the dendritic cell specific antibody in order to enhance the efficacy of the vaccine. In certain aspects the immune adjuvant may be a toll-like receptor (TLR) agonist. TLR agonists comprise flagellins from *Salmonella enterica* or *Vibrio cholerae*. TLR agonists may be specific for certain TLR classes (i.e., TLR2, TLR5, TLR7 or TLR9 agonists) and may be presented in any combination or as any modification. Examples of such immune adjuvants are described in U.S. application Ser. Nos. 13/208,993, 13/415,564, and in WO 2012/021834, the contents of all of which are incorporated herein by reference. US Patent Publications 2012/0039,916 and 2012/023,102 are incorporated by reference to the extent they disclose different TLR agonists.

In some embodiments, the compositions and fusion proteins comprising dendritic cell antibodies and HPV antigens are used to treat HPV related diseases or an HPV related pathology. In some embodiments, an HPV related disease is dysplasia, benign neoplasia, pre-malignant neoplasia or cancer (malignant neoplasia). In some embodiments, the tissue or organ affected by dysplasia, benign neoplasia, pre-malignant neoplasia or cancer is the cervix, vulva, vagina, penis, anus, oropharynx, head and neck, throat or lung. In some specific embodiments the HPV related diseases or an HPV related pathology is cervical intraepithelial neoplasia (CIN), vulvar intraepithelial neoplasia (VIN), penile intraepithelial neoplasia (PIN), and/or anal intraepithelial neoplasia (AIN). In still other embodiments, the compositions and fusion proteins comprising dendritic cell antibodies and HPV antigens are used to treat HPV related Common warts, Plantar warts, Flat warts, Anogenital warts, Anal lesions, Genital cancers, Epidermodysplasia verruciformis, Focal epithelial hyperplasia (oral), Oral papillomas, Oropharyngeal cancer, Verrucous cyst or Laryngeal papillomatosis.

III. METHODS OF TREATMENT

As discussed above, the compositions and methods of using these compositions can treat a subject (e.g., prevent an HPV infection or HPV related disease or evoke a robust or potentiate an immune response to HPV or HPV related disease) having, suspected of having, or at risk of developing an infection or related disease, related to HPV.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the invention in a recipient patient. Treatment or therapy can be an active immune response induced by administration of immunogen or a passive therapy effected by administration of a fusion protein composition, immunogenic composition or protein composition comprising an antibody/antigen fusion protein, antibody/antigen fusion protein containing material, or primed T-cells.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., 1994), by antigen-dependent killing (cytotoxic T lymphocyte assay, Tigges et al., 1996, incorporated by reference) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject. As used herein and in the claims, the terms "antibody" or "immunoglobulin" are used interchangeably.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In one embodiment a method includes treatment for a disease or condition caused by or suspected of being caused by an HPV pathogen. In certain aspects embodiments include methods of treatment of HPV infection, such as an infection acquired from an HPV positive individual. In some embodiments, the treatment is administered in the presence of HPV antigens. Furthermore, in some examples, treatment comprises administration of other agents commonly used against viral infection.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

Combination Therapy

The compositions and related methods, particularly administration of an antibody that binds DC receptor and delivers an HPV antigen or antigens or peptide or peptides to a patient/subject, may also be used in combination with the administration of traditional anti-viral therapies or anti-cancer therapies or drugs. These include, but are not limited to, entry inhibitors, CCR5 receptor antagonists, nucleoside reverse transcriptase inhibitors, nucleotide reverse transcriptase inhibitors, non-nucleoside reverse transcriptase inhibitors, protease inhibitors, integrase inhibitors and maturation inhibitors. Anti-cancer therapies include but are not limited to chemotherapy, radiotherapy or radiation therapy.

The compositions and related methods, particularly administration of an antibody that binds DC receptor and delivers an HPV antigen or antigens or peptide or peptides to a patient/subject, may also be used in combination with the administration of one or more anti-cancer drugs that include but are not limited to Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bleomycin, Bortezomib, Bosulif (Bosutinib), Bosutinib, Brentuximab Vedotin, Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, CeeNU (Lomustine), Cerubidine (Daunorubicin Hydrochloride), Cervarix (Recombinant HPV Bivalent Vaccine comprising recombinant L1 protein of HPV types 16 and 18), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine comprising recombinant L1 protein of HPV types 6, 11, 16, and 18), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Herceptin (Trastuzumab), HPV Bivalent Vaccine, Recombinant, HPV Quadrivalent Vaccine, Recombinant, Hycamtin (Topotecan Hydrochloride), Ibritumomab Tiuxetan, Ibrutinib, ICE, Iclusig (Ponatinib Hydrochloride), Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), OEPA, OPPA, Oxaliplatin, Paclitaxel, Paclitaxel Albumin-stabilized Nanoparticle Formulation, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Radium 223 Dichloride, Raloxifene Hydrochloride, Rasburicase, R-CHOP, R-CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid) and Zytiga (Abiraterone Acetate).

The compositions and related methods, particularly administration of an antibody that binds DC receptor and delivers an HPV antigen or antigens or peptide or peptides to a patient/subject, may also be used in combination with the administration of radiation therapy that includes but is not limited to X-rays, gamma rays, and charged particles. The radiation may be delivered by a machine outside the body (external-beam radiation therapy), or it may come from radioactive material placed in the body near cancer cells (internal radiation therapy or brachytherapy). Internal radiation therapy may be systemic (e.g. radioactive iodine). External-beam radiation therapy may include, but is not limited to, 3-dimensional conformal radiation therapy (3D-CRT), Intensity-modulated radiation therapy (IMRT), Image-guided radiation therapy (IGRT), Tomotherapy, Stereotactic radiosurgery (SRS), Stereotactic body radiation therapy (SBRT), Proton therapy or other charged particle beams (e.g., electron beams). Internal radiation therapy or brachytherapy may comprise interstitial brachytherapy which uses a radiation source placed within tumor tissue and may be used to deliver a dose higher than external beam radiation while causing less damage to normal tissue. Brachytherapy may be given as a low-dose rate or high-dose rate treatment. In additional embodiments, brachytherapy may be permanent or temporary. Radiation therapy may comprise systemic radiation therapy. Systemic radiation therapy may comprise a swallowed or injected radioactive substance, that includes, but is not limited to any single, multiple or combination dose of Radioactive iodine ($^{131}$I), ibritumomabtiuxetan (Zevalin®), 131 tositumomab (Bexxar®), samarium-153-lexidronam (Quadramet®) and strontium-89 chloride (Metastron®) or any monoclonal bound to a radioactive substance. The dose of radiation according to different embodiments may be tailored to the specific disease, condition or cancered being treated. In some embodiments, the single or total dose may be 1-10 gray (Gy), 10-20 Gy, 20-40 Gy, 40-60 Gy, or 60-80 Gy, or any value or rage derivable therein. In some embodiments, radiation therapy or dose may be fractionated. In one embodiment, a total dose may be fractionated per day or per week. In certain embodiments the daily fractionated dose may be 1.8-2 Gy. It is contemplated that a total dose may be fractionated into daily or weekly doses in the range of 0.1 Gy to 10 Gy.

In one aspect, it is contemplated that a therapy is used in conjunction with antiviral or anti-cancer therapies. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In yet another aspect, a vaccine may be administered as part of a prime/boost strategy. A priming vaccine dose can be administered using a DC specific antibody fused to an HPV antigen in any of the embodiments described herein. A vaccine boost can be administered through the use of a second vaccine, either of the same type or from a different type of vaccine. Examples of a separate HPV vaccine include Gardasil™ (recombinant HPV quadrivalent vaccine comprising recombinant L1 protein of HPV types 6, 11, 16, and 18) or Cervarix™ (recombinant HPV bivalent vaccine comprising recombinant L1 protein of HPV types 16 and 18). Additional examples of such different vaccines include naked DNA vaccines or a recombinant viruses. The second vaccine may comprise additional HPV antigens apart from the E6 or E7 antigens that may be used in the first vaccine. It is also contemplated that the second vaccine may comprise an HPV protein such as an E6 or E7 protein plus an adjuvant either directly linked or administered independently.

Various combinations of therapy may be employed, for example antiviral or anti-cancer therapy is "A" and an antibody vaccine that comprises an antibody that binds a DC receptor and delivers an HPV antigen or a peptide or consensus peptide thereof is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

General Pharmaceutical Compositions

In some embodiments, pharmaceutical compositions are administered to a subject. Different aspects may involve administering an effective amount of a composition to a subject. In some embodiments, an antibody that binds DC receptor and delivers an HPV antigen or a peptide or consensus peptide thereof may be administered to the patient to protect against or treat infection by one or more HPV types or protect or treat against one or more HPV related diseases such as cancer. Alternatively, an expression vector encoding one or more such antibodies or polypeptides or peptides may be given to a patient as a preventative treatment. Additionally, such compositions can be administered in combination with an antibiotic, antiviral or anticancer agent. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the mucosal, intravenous, intramuscular, sub-cutaneous, intratumoral or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intratumoral, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 4:
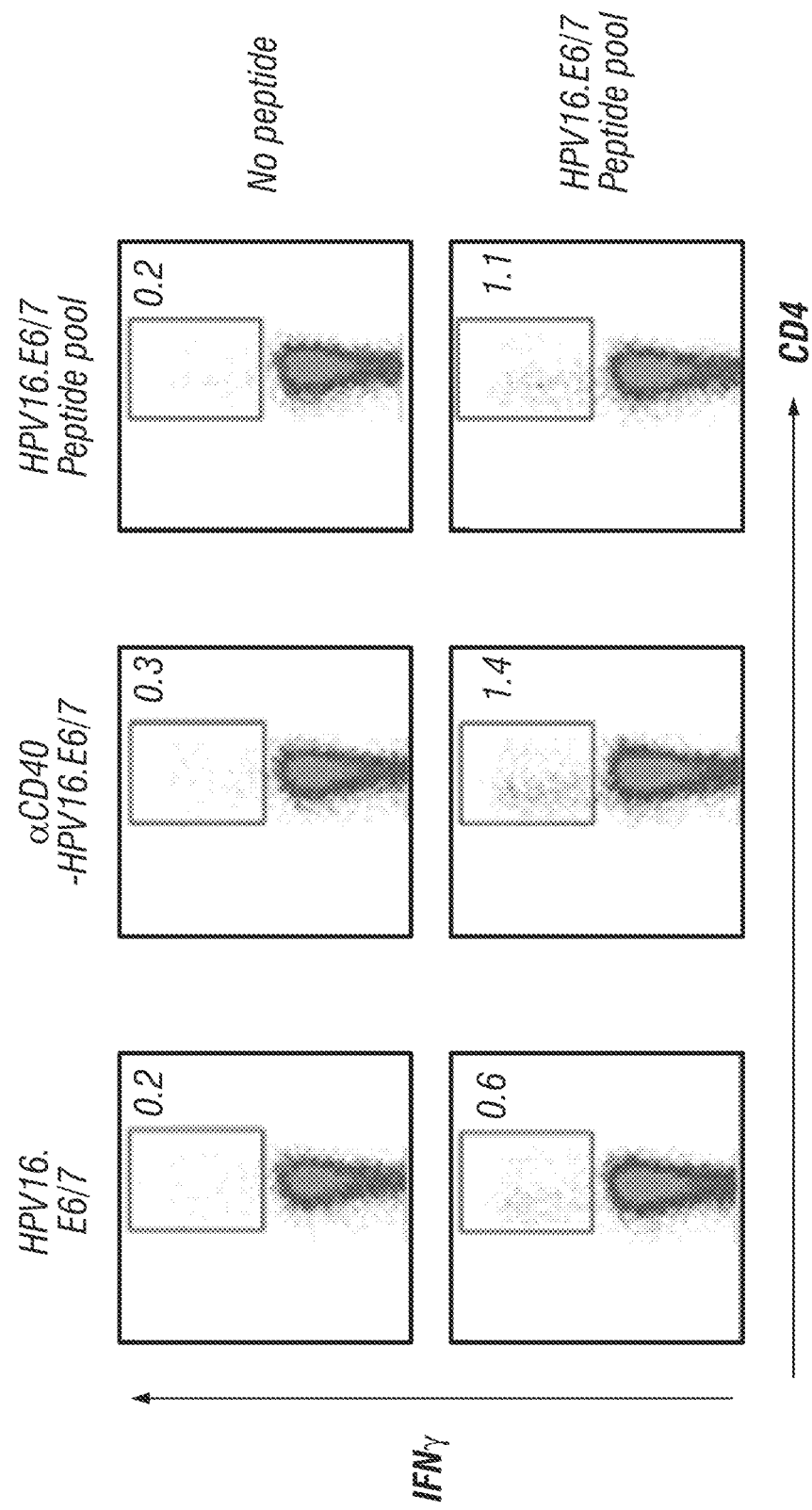
FIG. 4: Anti-CD40-HPV16.E6/7 can elicit HPV16.E6/7-specific CD4+ and CD8+ T-cell responses.
Figure 4:
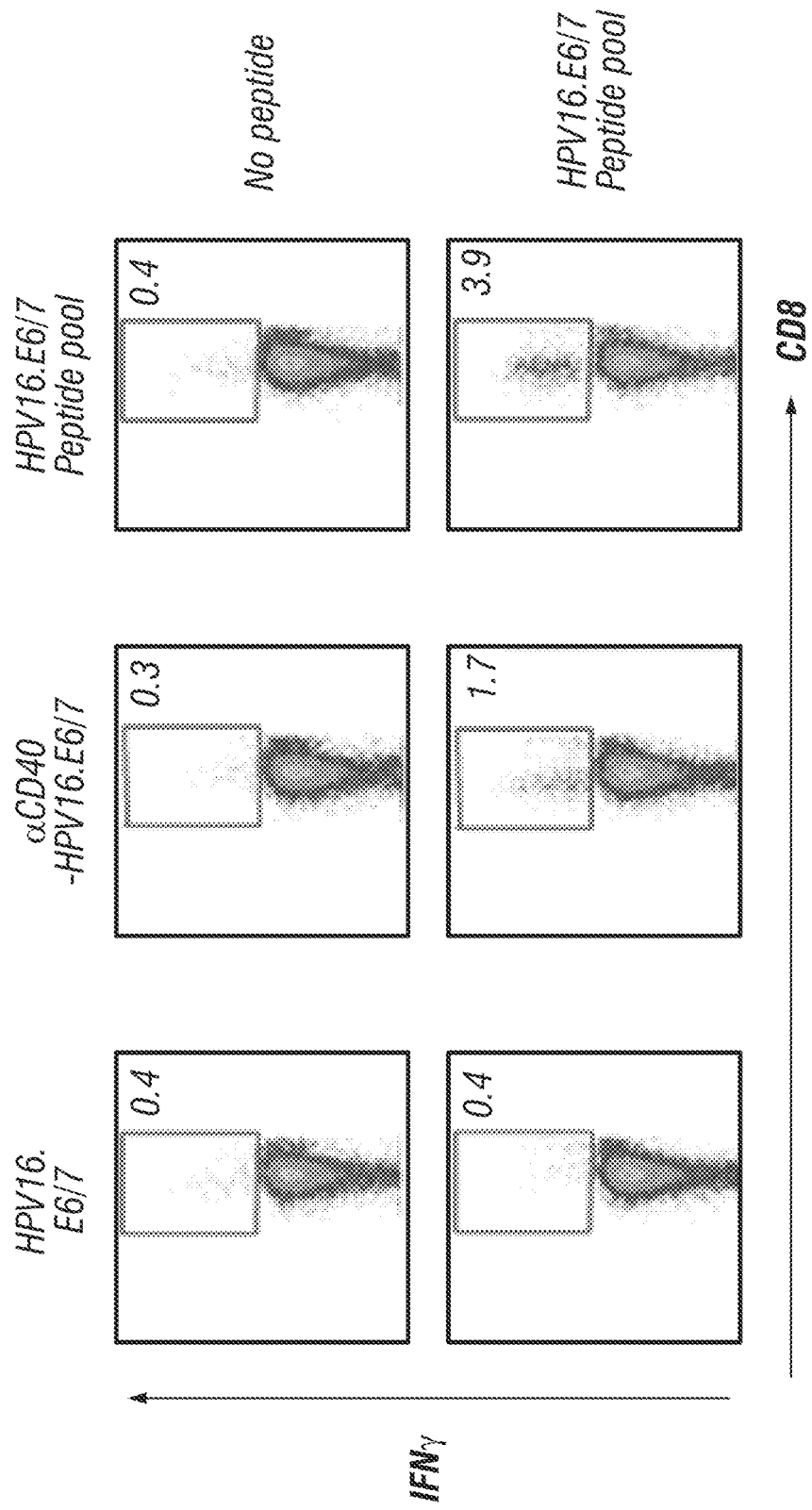

Example 1—Recombinant Fusion Proteins of Anti-DC Receptors (DCRs) and HPV E6 and E6 Fusion Proteins The inventors' scheme for the development of expression constructs for production of anti-DC receptor antibodies fused to E6 and E7 sequences from HPV 16 and 18 is given in FIG. 1. The scheme identifies an order of antigen cassettes encoding E6 and E7 from HPV 16 and 18 that is efficiently secreted and are intact when fused to the H chain C-terminus. There are 64 possible combinations of just these 4 sequences, and very many more when interspersed with flexible linker sequences. The inventors' strategy is a stepwise approach starting with each antigen alone, with and without a preceding flexible linker [8 initial constructs], then selecting those vectors that express most efficiently for adding on additional cassettes. Each cycle of construction and testing takes one week. Establishing the final production CHO-S cell lines take a further 8 weeks, including scale-up to levels suitable for vaccine production to preclinical studies in human in vitro and animal in vivo.

A transient expression vector encoding the antibody heavy chain has an in-frame Nhe I site at the C-terminus and antigen or flexible linker encoding Spe I-Not I cassettes are inserted between the vector Nhe I and Not I sites. The vector Nhe I site is lost in this ligation, but each cassette encodes a new C-terminal in-frame Nhe I site. Thus, additional antigen or linker cassettes can be added in an iterative fashion. Each new construct is transiently transfected into 293F cells with a matching light chain vector and at 72 hr secreted vaccine is isolated by protein A affinity and analyzed by SDS.PAGE. Constructs that express well are the preferred vectors for adding new cassettes (FIG. 1).

The inventors have engineered expression constructs with HPV16 E6 and E7 and HPV18 E6 and E7 sequences fused to antibody heavy chain C-terminii. Constructs with HPV16 or HPV18 E6 or HPV16 or HPV18 E7 sequences fused directly to an anti-dendritic cell receptor antibody heavy chain C-terminal codon failed to be secrete any detectable vaccine when co-transfected into 293F cells with a matching light chain expression vector (not shown). However, similar vectors incorporating a flexible linker sequence (Flex v1), secreted the vaccines (FIG. 2, lanes 1 and 3). Furthermore, constructs adding HPV E6 onto the Flex v1 HPV E7 vector and vice versa, also secreted vaccine (FIG. 2, lanes 2 and 4). Successful expression of such vaccines is independent on the variable region sequences. Thus, the Flex v1-HPV E6/E7 sequence was transferred to established vectors for stable expression of anti-CD40-Flex v1-HPV16 or 18 E6-HPV16E7, anti-Langerin-Flex v1-HPV16 or 18 E6-HPV16E7 and control hIgG4-Flex-v1-HPV16 or 18 E6-HPV16E7 in CHO-S cells.

Anti-CD40-HPV16.E6/7 can efficiently bind to DCs in peripheral blood of healthy donors. Peripheral blood mononuclear cells (PBMCs) were acquired from the blood of healthy individuals. PBMCs were incubated for 15 min on ice in the presence of different amounts of anti-CD40-HPV16.E6/7 or control IgG4-HPV16.E6/7 proteins. Cells were washed vigorously and then stained with anti-E6/7 antibodies to detect cell surface bound proteins. As shown in FIG. 3, anti-CD40-HPV16.E6/7 can efficiently bind to human blood DCs (CD3-CD19-CD14-HLA-DR+CD11c+). In contrast, IgG4-HPV16.E6/7 did not bind to the same DCs. Anti-CD40-HPV18.E6/7 also bound to DCs in peripheral blood of healthy donors (data not shown).

Anti-CD40-HPV16.E6/7 can efficiently activate E6/7-specific memory CD4+ and CD8+ T cells from HPV-related cancer patients. Evaluated next was the in vitro immunogenicity of anti-CD40-HPV16.E6/7 using PBMCs from HPV-positive head and neck cancer patients. Patient PBMCs were loaded with recombinant HPV16.E6/7 proteins, anti-CD40-HPV16.E6/7, or peptide pool of HPV16.E6/7 proteins. In this experiment, the same molar concentration of E6/7 in each protein was applied to compare the levels of E6/7-specific IFNg-expressing CD4+ and CD8+ T cell responses. After 7 days in vitro culture, PBMCs were restimulated for 5 h with peptide pool of E6/7 in the presence of brefeldin A and then cells were stained for IFNg expression. FIG. 4 shows that anti-CD40-HPV16.E6/7 was more efficient than HPV16.E6/7 at eliciting IFNg+CD4+ and IFNg+CD8+ T cell responses. The levels of HPV16.E6/7-specific IFNg+CD4+ T cell responses elicited with anti-CD40-HPV16.E6/7 was similar to those elicited by the peptide pool that was used as a positive control. Thus, our new vaccine models composed of anti-DCR and HPV antigens, including E6/7, is highly effective in activating antigen-specific cellular immune responses in the patients who have HPV-related cancers. Furthermore, such HPV antigen (E6 and E7)-specific CD8+ CTLs are expected to efficiently suppress tumor progression and could result in the rejection of tumors in patients.

Figure 5:
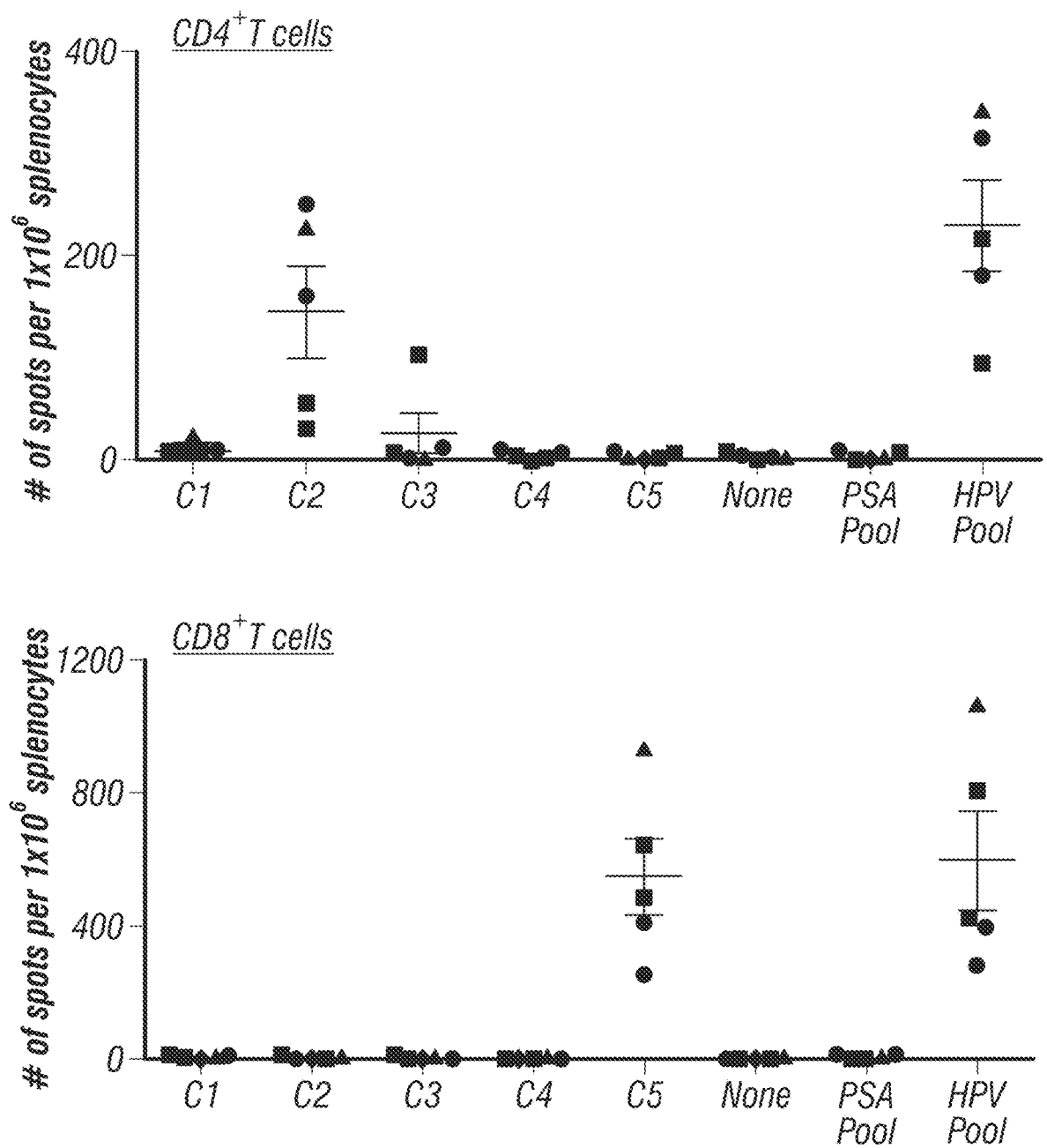
FIG. 5: Anti-CD40-HPV16.E6/7 can efficiently induce HPV16.E6/7-specific CD4+ and CD8+ T-cell responses.

Anti-CD40-HPV16.E6/7 can prime E6/7-specific CD4+ and CD8+ T cell responses in vivo. To test the in vivo immunogenicity of anti-CD40-HPV16.E6/7 vaccine, human CD40 transgenic mice were used. Five animals were immunized s.c. with 30 ug anti-CD40-HPV16.E6/7 plus poly IC on day 0 and then boosted twice with the same vaccine. On day 7 after the second boosting, CD4+ and CD8+ T cells were purified from spleens and then restimulated with one of HPV16.E6/7 peptide clusters 1-5, none, a peptide pool of prostate specific antigen (PSA), or a HPV16.E6/7 peptide pool. FIG. 5 shows that anti-CD40– HPV16.E6/7 induce HPV16 E6/7 peptide clusters 2 and 3-specific CD4+ and cluster 5-specific CD8+ T cell responses in the human CD40 transgenic mice. Importantly, the levels of E6/7-specific CD8+ T cell responses were greater than the levels of E6/7-specific CD4+ T cell responses. This indicates that anti-CD40–HPV16.E6/7 vaccines are particularly efficient in eliciting CD8+ CTLs that can kill HPV-infected cells and tumor cells. Each dot in FIG. 5 represent the data generated with a single mouse.

Figure 6:
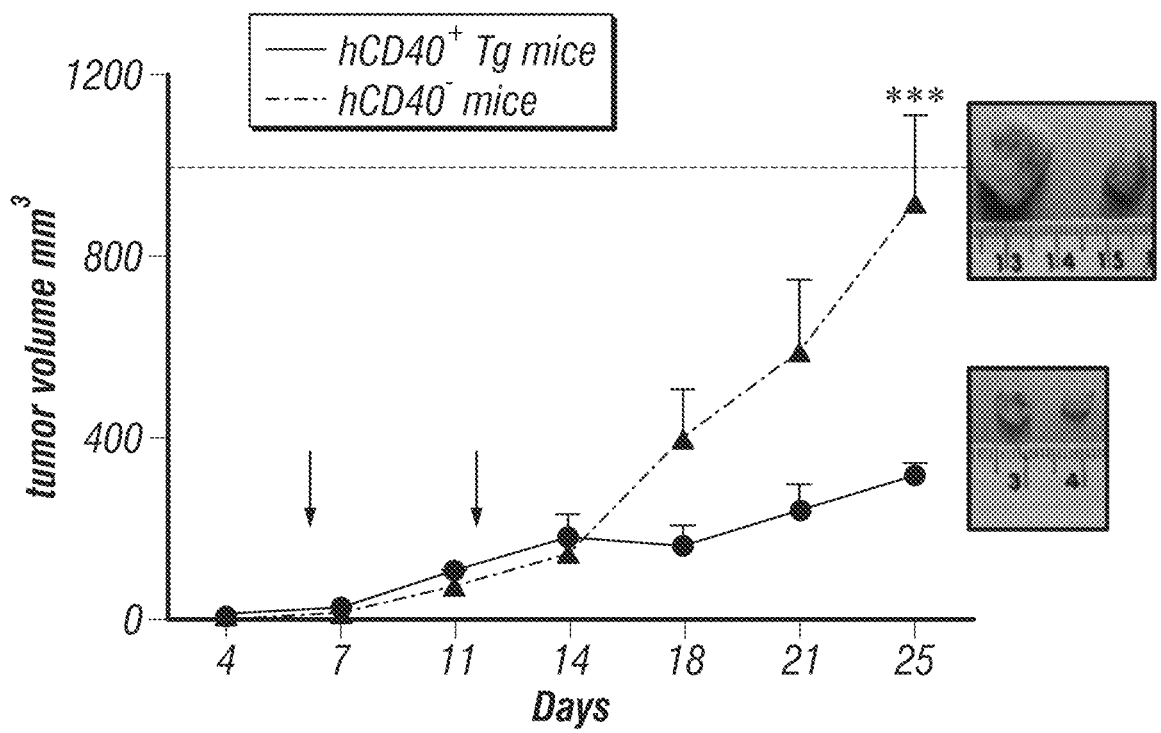
FIG. 6: Anti-CD40-HPV16.E6/7 can suppress TC-1 tumor progression in human CD40Tg mice.

Anti-CD40-HPV16.E6/7 can suppress TC-1 tumor progression in the human CD40 transgenic mice. Efficacy of anti-CD40-HPV16.E6/7 plus poly IC vaccine was tested in TC-1 challenged human CD40 transgenic mice. Two groups of animals (Human CD40+ and human CD40– mice, 5 mice per group) were challenged on day 0 with TC-1 tumor cell line subcutaneously. On days 6 and 12, animals were immunized with anti-CD40– HPV.E6/7 plus poly IC. Tumor progression was assessed and presented in FIG. 6. By day 14 after TC-1 challenge, both human CD40+ and CD40– mice developed similar sizes of tumors. In the human CD40– animals TC-1 tumor progressed quickly and reached 1000 mm$^3$ on day 25 after the challenge. However, TC-1 tumor progression in the human CD40+ mice was significantly delayed. Our data demonstrate that anti-CD40-HPV16.E6/7 vaccine targets human CD40 and thus elicits E6/7-specific CD8+ CTLs, as shown in FIG. 5, that suppress TC-1 tumor progression in the animals.

Figure 7:
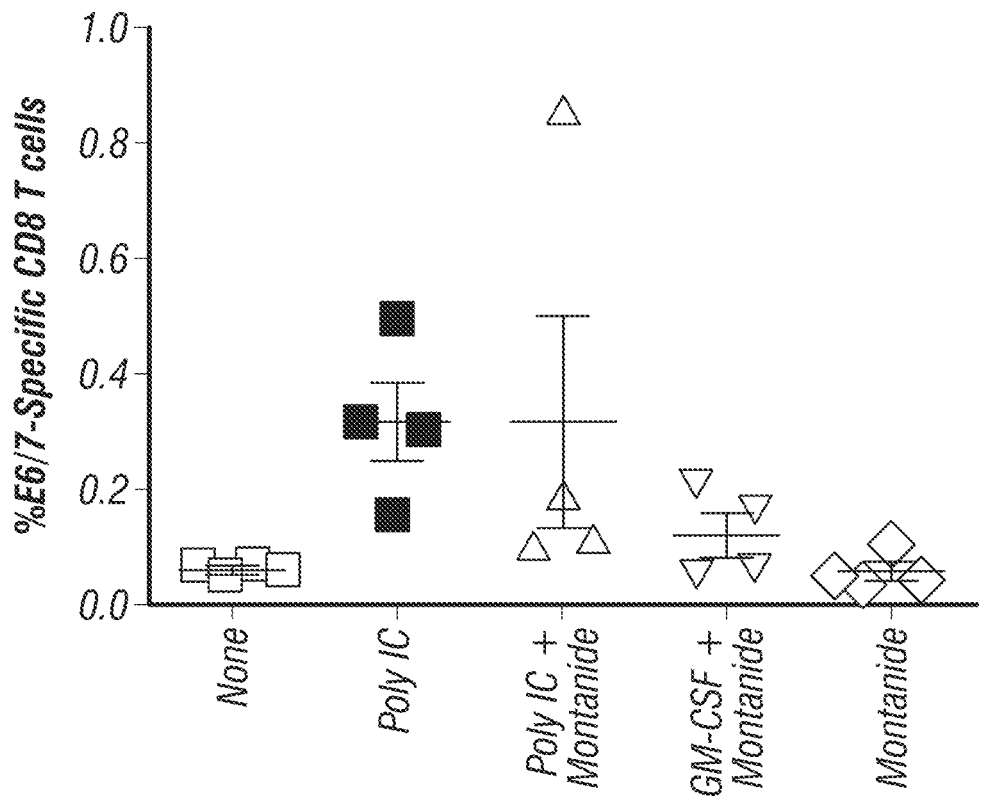
FIG. 7: Effect of adjuvant co-administration with anti-CD40-HPV16.E6/7.

The effects of poly IC, poly IC plus montanide, GM-CSF plus montanide, and montanide alone on the immunogenicity of anti-CD40-HPV.E6/7 vaccine was tested in the human CD40 transgenic mice. Four animals in each group were immunized s.c. with 30 ug anti-CD40-HPV.E6/7 alone or anti-CD40-HPV16.E6/7 with indicated adjuvants (FIG. 7). After 7 days, blood from individual animals were harvested and stained with tetramer. As shown in the figure below, poly IC was able to effectively promote anti-CD40-HPV16.E6/7-specific CD8+ T cell responses. Montanide alone or GM-CSF in montanide did not significantly promote E6/7-specific CD8+ T cell responses.

Sequences below are based on the humanized 12E12 anti-human CD40 VK2 VH2 antibody—protein sequences are the expected mature secreted protein sequence and the DNA sequences include the initiator ATG and the leader peptide region. Alternately, the HPV18 sequences can be grafted onto the C-terminus of the VK2 chain and a broader spectrum vaccine produced by combining this with the HPV16 sequences on the VH2 H chain.

| | | |
|---|---|---|
| HPV 16 E6 | see below | SEQ ID NO: 1 |
| HPV 16 E7 | see below | SEQ ID NO: 2 |
| HPV 18 E6 | see below | SEQ ID NO: 3 |
| HPV 18 E7 | see below | SEQ ID NO: 4 |
| Flexv1 | see below | SEQ ID NO: 5 |
| f1 | see below | SEQ ID NO: 6 |
| hAnti-CD40VK2-LV-hIgGK-C | see below | SEQ ID NO: 7 |
| hAnti-CD40VH2-LV-hIgG4H-C | see below | SEQ ID NO: 8 |
| Anti-CD4012E12 light chain variable region | see below | SEQ ID NO: 9 |
| Anti-CD4012E12 heavy chain variable region | see below | SEQ ID NO: 10 |
| Anti-CD40 12E12 CDR1L | SASQGISNYLN | SEQ ID NO: 11 |
| Anti-CD40 12E12 CDR2L | YTSILHS | SEQ ID NO: 12 |
| Anti-CD40 12E12 CDR3L | QQFNKLPPT | SEQ ID NO: 13 |
| Anti-CD40 12E12 CDR1H | GFTFSDYYMY | SEQ ID NO: 14 |
| Anti-CD40 12E12 CDR2H | YINSGGGSTYYPDTVKG | SEQ ID NO: 15 |
| Anti-CD40 12E12 CDR3H | RGLPFHAMDY | SEQ ID NO: 16 |

HPV 16 E6

(SEQ ID NO: 1)
MHQKRTAMFQDPQERPRKLPQLCTELQTTIHDIILECVYCKQQLLRREV
GDFAFRDLCIVYRDGNPYAVCDKCLKFYSKISEYRHYCYSVYGTTLEQQ
YNKPLCDLLIRCINCQKPLCPE

HPV 16 E7

(SEQ ID NO: 2)
MHGDTPTLHEYMLDLQPETTDLYGYGQLNDSSEEEDEIDGPAGQAEPDR
AHYNIVTFCCK

HPV 18 E6

(SEQ ID NO: 3)
MARFEDPTRRPYKLPDLCTELNTSLQDIEITCVYCKTVLELTEVGEFAF
KDLFVVYRDSIPHAACHKCIDFYSRIRELRHYSDSVYGDTLEKLTNTGL
YNLLIRCLRCQKPLNP

HPV 18 E7

(SEQ ID NO: 4)
MHGPKATLQDIVLHLEPQNEIPVDLLGHGQLSDSEEENDEIDGVNHQHL
PARRAEPQRHTMLCMCCK

Flexv1

(SEQ ID NO: 5)
QTPTNTISVTPTNNSTPTNNSNPKPNP f1

(SEQ ID NO: 6)
SSVSPTTSVHPTPTSVPPTPTKSSP hAnti-CD40VK2-LV-hIgGK-C
(SEQ ID NO: 7)
DIQMTQSPSSLSASVGDRVTITCSASQGISNYLNWYQQKPGKAVKLLIY
YTSILHSGVPSRFSGSGSGTDYTLTISSLQPEDFATYYCQQFNKLPPTF
GGGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC hAnti-CD40VH2-LV-hIgG4H-C
(SEQ ID NO: 8)
EVKLVESGGGLVQPGGSLKLSCATSGFTFSDYYMYWVRQAPGKGLEWVA
YINSGGGSTYYPDTVKGRFTISRDNAKNTLYLQMNSLRAEDTAVYYCAR
RGLPFHAMDYWGQGTLVTVSSAKTKGPSVFPLAPCSRSTSESTAALGCL
VKDYFPEPVTVSWNSGALTSGVHTFPAVLQSSGLYSLSSVVTVPSSSLG
TKTYTCNVDHKPSNTKVDKRVESKYGPPCPPCPAPEFEGGPSVFLFPPK
PKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKT
TPPVLDSDGSFFLYSRLTVDKSRWQEGNVFSCSVMHEALHNHYTQKSLS
LSLGK Anti-CD4012E12 light chain variable region
(SEQ ID NO: 9)
DIQMTQTTSSLSASLGDRVTISCSASQGISNYLNWYQQKPDGTVKLLIY
YTSILHSGVPSRFSGSGSGTDYSLTIGNLEPEDIATYYCQQFNKLPPTF
GGGTKLEIK Anti-CD4012E12 heavy chain variable region
(SEQ ID NO: 10)
CEVKLVESGGGLVQPGGSLKLSCATSGFTFSDYYMYWVRQTPEKRLEWV
AYINSGGGSTYYPDTVKGRFTISRDNAKNTLYLQMSRLKSEDTAMYYCA
RRGLPFHAMDYWGQGTSVTVS hAnti-CD40VK2-LV-hIgGK-C
(SEQ ID NO: 17)
DIQMTQSPSSLSASVGDRVTITCSASQGISNYLNWYQQKPGKAVKLLIY

YTSILHSGVPSRFSGSGSGTDYTLTISSLQPEDFATYYCQQFNKLPPTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC hAnti-CD40VK2-LV-hIgGK-C DNA sequence (includes
the leader peptide region)
(SEQ ID NO: 18)
ATGAGGGTCCCCGCTCAGCTCCTGGGGCTCCTGCTGCTCTGGCTCCCAG

GCGCGCGATGTGATATCCAGATGACACAGAGCCCTTCCTCCCTGTCTGC

CTCTGTGGGAGACAGAGTCACCATCACCTGCAGTGCAAGTCAGGGCATT

AGCAATTATTTAAACTGGTATCAGCAGAAACCAGGCAAGGCCGTTAAAC

TCCTGATCTATTACACATCAATTTTACACTCAGGAGTCCCATCAAGGTT

CAGTGGCAGTGGGTCTGGGACAGATTATACCCTCACCATCAGCTCCCTG

CAGCCTGAAGATTTCGCCACTTACTATTGTCAGCAGTTTAATAAGCTTC

CTCCGACGTTCGGTGGAGGCACCAAACTCGAGATCAAACGAACTGTGGC

TGCACCATCTGTCTTCATCTTCCCGCCATCTGATGAGCAGTTGAAATCT

GGAACTGCCTCTGTTGTGTGCCTGCTGAATAACTTCTATCCCAGAGAGG

CCAAAGTACAGTGGAAGGTGGATAACGCCCTCCAATCGGGTAACTCCCA

GGAGAGTGTCACAGAGCAGGACAGCAAGGACAGCACCTACAGCCTCAGC

AGCACCCTGACGCTGAGCAAAGCAGACTACGAGAAACACAAAGTCTATG

CCTGCGAAGTCACCCATCAGGGCCTGAGCTCGCCCGTCACAAAGAGCTT

CAACAGGGGAGAGTGTTAG hAnti-CD40VH2-LV-hIgG4H-C-Flex-v1-HPV16-E6-HPV16-E7-f1
(SEQ ID NO: 19)
EVKLVESGGGLVQPGGSLKLSCATSGFTFSDYYMYWVRQAPGKGLEWVAYINSGG

GSTYYPDTVKGRFTISRDNAKNTLYLQMNSLRAEDTAVYYCARRGLPFHAMDYWG

QGTLVTVSSAKTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGKAS<u>QTPTN</u>

<u>YISVYPYNNSYPYNNSNPKPNPASMHQKRTAMFQDPQERPRKLPQLCTELQTTIHDII</u>

-continued

*<u>LECVYCKQQLLRREVGDFAFRDLCIVYRDGNPYAVCDKCLKFYSKISEYRHYCYSVY</u>*

*<u>GTTLEQQYNKPLCDLLIRCINCQKPLCPE</u>*AS*<u><u>MHGDTPTLHEYMLDLQPETTDLYGYG</u></u>*

*<u><u>QLNDSSEEEDEIDGPAGQAEPDRAHYNIVTFCCK</u></u>*AS<u>SSVSPYYSVHPYPYSVPPYPYKS</u>

<u>SPAS</u>
(Bold, italicized single underline sequence is HPV16 E6; bold, italicized
double underline sequence is HPV16 E7; non-bolded, non-italicized single
underlined (Flexv1) and non-bolded, non-italicized double underlined (f1)
sequences are flexible glycosylated linker sequences)

hAnti-CD40VH2-LV-hIgG4H-C-Flex-v1-HPV16-E6-HPV16-E7-f1 DNA sequence
(includes the leader peptide region)

(SEQ ID NO: 20)

*AT*GGGTTGGAGCCTCATCTTGCTCTTCCTTGTCGCTGTTGCTACGCGTGTCCACTC

CGAAGTGAAGCTGGTGGAGTCTGGGGGAGGCTTAGTGCAGCCCGGAGGGTCCCT

GAAACTCTCCTGTGCAACCTCTGGATTCACTTTCAGTGACTATTACATGTATTGGG

TTCGCCAGGCCCCAGGCAAGGGCCTGGAGTGGGTCGCATACATTAATTCTGGTGG

TGGTAGCACCTATTATCCAGACACTGTAAAGGGCCGATTCACCATCTCCAGAGAC

AATGCCAAGAACACCCTGTACCTGCAAATGAACAGCCTGAGGGCCGAGGACACA

GCCGTGTATTACTGTGCAAGACGGGGGTTACCGTTCCATGCTATGGACTATTGGG

GTCAAGGAACCCTGGTCACCGTCTCCTCAGCCAAAACGAAGGGCCCATCCGTCTT

CCCCCTGGCGCCCTGCTCCAGGAGCACCTCCGAGAGCACAGCCGCCCTGGGCTGC

CTGGTCAAGGACTACTTCCCCGAACCGGTGACGGTGTCGTGGAACTCAGGCGCCC

TGACCAGCGGCGTGCACACCTTCCCGGCTGTCCTACAGTCCTCAGGACTCTACTC

CCTCAGCAGCGTGGTGACCGTGCCCTCCAGCAGCTTGGGCACGAAGACCTACAC

CTGCAACGTAGATCACAAGCCCAGCAACACCAAGGTGGACAAGAGAGTTGAGTC

CAAATATGGTCCCCCATGCCCACCCTGCCCAGCACCTGAGTTCGAAGGGGGACC

ATCAGTCTTCCTGTTCCCCCCAAAACCCAAGGACACTCTCATGATCTCCCGGACC

CCTGAGGTCACGTGCGTGGTGGTGGACGTGAGCCAGGAAGACCCCGAGGTCCAG

TTCAACTGGTACGTGGATGGCGTGGAGGTGCATAATGCCAAGACAAAGCCGCGG

GAGGAGCAGTTCAACAGCACGTACCGTGTGGTCAGCGTCCTCACCGTCCTGCACC

AGGACTGGCTGAACGGCAAGGAGTACAAGTGCAAGGTCTCCAACAAAGGCCTCC

CGTCCTCCATCGAGAAAACCATCTCCAAAGCCAAAGGGCAGCCCCGAGAGCCAC

AGGTGTACACCCTGCCCCCATCCCAGGAGGAGATGACCAAGAACCAGGTCAGCC

TGACCTGCCTGGTCAAAGGCTTCTACCCCAGCGACATCGCCGTGGAGTGGGAGA

GCAATGGGCAGCCGGAGAACAACTACAAGACCACGCCTCCCGTGCTGGACTCCG

ACGGCTCCTTCTTCCTCTACAGCAGGCTAACCGTGGACAAGAGCAGGTGGCAGG

AGGGGAATGTCTTCTCATGCTCCGTGATGCATGAGGCTCTGCACAACCACTACAC

ACAGAAGAGCCTCTCCCTGTCTCTGGGTAAAGCTAGTCAGACCCCCACCAACACC

ATCAGCGTGACCCCCACCAACAACAGCACCCCCACCAACAACAGCAACCCCAAG

CCCAACCCCGCTAGTATGCACCAAAAAAGGACCGCAATGTTTCAGGACCCCCAA

GAGAGGCCCCGCAAACTGCCACAACTTTGCACGGAGCTGCAGACAACAATACAT

GACATCATTCTCGAATGTGTTTACTGTAAGCAGCAGTTGTTGCGAAGAGAAGTGG

GAGACTTCGCTTTCAGAGACCTGTGTATCGTATATCGCGATGGCAATCCTTATGC

CGTCTGCGATAAATGCCTCAAGTTTTACTCCAAGATCAGCGAGTACCGGCACTAC

-continued

```
TGTTACTCTGTGTATGGGACTACCCTCGAACAGCAGTATAACAAGCCGCTGTGCG

ATCTCCTTATCCGGTGCATTAACTGCCAGAAGCCACTGTGTCCTGAGGCTAGTAT

GCACGGGGATACCCCCACACTCCACGAATACATGCTTGATTTGCAACCTGAAACG

ACCGACCTGTACGGCTATGGTCAGCTGAATGACTCCAGCGAGGAAGAGGATGAG

ATTGACGGACCGGCAGGCCAGGCCGAGCCAGACCGGGCTCATTATAACATCGTG

ACTTTCTGCTGTAAGGCTAGTAGCAGCGTGAGCCCCACCACCAGCGTGCACCCCA

CCCCCACCAGCGTGCCCCCCACCCCCACCAAGAGCAGCCCCGCTAGCTGA
``` hAnti-CD40VH2-LV-hIgG4H-C-Flex-v1-HPV18E6-HPV18E7-f1
(SEQ ID NO: 21)

EVKLVESGGGLVQPGGSLKLSCATSGFTFSDYYMYWVRQAPGKGLEWVAYINSGG

GSTYYPDTVKGRFTISRDNAKNTLYLQMNSLRAEDTAVYYCARRGLPFHAMDYWG

QGTLVTVSSAKTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGKAS<u>QTPTN</u>

<u>YISNYPYNNSYPYNNSNPKPNPAS</u>*MARFEDPTRRPYKLPDLCTELNTSLQDIEITCVYC*

*KTVLELTEVGEFAFKDLFVVYRDSIPHAACHKCIDFYSRIRELRHYSDSVYGDTLEKL*

*TNTGLYNLLIRCLRCQKPLNPA*<u>S</u>*<u>MHGPKATLQDIVLHLEPQNEIPVDLLGHGQLSDS</u>*

*<u>EEENDEIDGVNHQHLPARRAEPQRHTMLCMCCK</u>*AS<u>SSVSPTTSVHPYPYSVPPYPYK</u>

<u>SSPAS</u>
(Bold, italicized single underline sequence is HPV18 E6; bold, italicized
double underline sequence is HPV18 E7; non-bolded, non-italicized single
underlined (Flexv1) and non-bolded, non-italicized double underlined (f1)
sequences are flexible glycosylated linker sequences)

hAnti-CD40VH2-LV-hIgG4H-C-Flex-v1-HPV18E6-HPV18E7-f1 DNA sequence
(includes the leader peptide region)
(SEQ ID NO: 22)

ATGGGTTGGAGCCTCATCTTGCTCTTCCTTGTCGCTGTTGCTACGCGTGTCCACTC

CGAAGTGAAGCTGGTGGAGTCTGGGGGAGGCTTAGTGCAGCCCGGAGGGTCCCT

GAAACTCTCCTGTGCAACCTCTGGATTCACTTTCAGTGACTATTACATGTATTGGG

TTCGCCAGGCCCCAGGCAAGGGCCTGGAGTGGGTCGCATACATTAATTCTGGTGG

TGGTAGCACCTATTATCCAGACACTGTAAAGGGCCGATTCACCATCTCCAGAGAC

AATGCCAAGAACACCCTGTACCTGCAAATGAACAGCCTGAGGGCCGAGGACACA

GCCGTGTATTACTGTGCAAGACGGGGGTTACCGTTCCATGCTATGGACTATTGGG

GTCAAGGAACCCTGGTCACCGTCTCCTCAGCCAAAACGAAGGGCCCATCCGTCTT

CCCCCTGGCGCCCTGCTCCAGGAGCACCTCCGAGAGCACAGCCGCCCTGGGCTGC

CTGGTCAAGGACTACTTCCCCGAACCGGTGACGGTGTCGTGGAACTCAGGCGCCC

TGACCAGCGGCGTGCACACCTTCCCGGCTGTCCTACAGTCCTCAGGACTCTACTC

CCTCAGCAGCGTGGTGACCGTGCCCTCCAGCAGCTTGGGCACGAAGACCTACAC

CTGCAACGTAGATCACAAGCCCAGCAACACCAAGGTGGACAAGAGAGTTGAGTC

-continued

```
CAAATATGGTCCCCCATGCCCACCCTGCCCAGCACCTGAGTTCGAAGGGGGACC

ATCAGTCTTCCTGTTCCCCCCAAAACCCAAGGACACTCTCATGATCTCCCGGACC

CCTGAGGTCACGTGCGTGGTGGTGGACGTGAGCCAGGAAGACCCCGAGGTCCAG

TTCAACTGGTACGTGGATGGCGTGGAGGTGCATAATGCCAAGACAAAGCCGCGG

GAGGAGCAGTTCAACAGCACGTACCGTGTGGTCAGCGTCCTCACCGTCCTGCACC

AGGACTGGCTGAACGGCAAGGAGTACAAGTGCAAGGTCTCCAACAAAGGCCTCC

CGTCCTCCATCGAGAAAACCATCTCCAAAGCCAAAGGGCAGCCCCGAGAGCCAC

AGGTGTACACCCTGCCCCCATCCCAGGAGGAGATGACCAAGAACCAGGTCAGCC

TGACCTGCCTGGTCAAAGGCTTCTACCCCAGCGACATCGCCGTGGAGTGGGAGA

GCAATGGGCAGCCGGAGAACAACTACAAGACCACGCCTCCCGTGCTGGACTCCG

ACGGCTCCTTCTTCCTCTACAGCAGGCTAACCGTGGACAAGAGCAGGTGGCAGG

AGGGGAATGTCTTCTCATGCTCCGTGATGCATGAGGCTCTGCACAACCACTACAC

ACAGAAGAGCCTCTCCCTGTCTCTGGGTAAAGCTAGTCAGACCCCCACCAACACC

ATCAGCGTGACCCCCACCAACAACAGCACCCCCACCAACAACAGCAACCCCAAG

CCCAACCCCGCTAGTATGGCCAGATTCGAGGATCCAACACGCCGACCTTACAAAT

TGCCGGACCTTTGCACGGAGCTGAACACTTCCCTGCAGGACATAGAAATTACCTG

CGTCTACTGCAAGACCGTTCTCGAACTGACAGAAGTAGGCGAGTTTGCGTTTAAA

GATCTGTTCGTGGTGTATCGGGATAGCATTCCCCACGCAGCTTGTCATAAGTGTA

TCGACTTCTATTCTAGGATCCGGGAGCTCAGACACTATAGCGATTCCGTGTACGG

CGACACACTTGAGAAGCTCACTAACACCGGGCTGTACAACCTCCTGATCCGGTGC

TTGAGGTGTCAGAAACCCCTGAATCCTGCTAGTATGCACGGGCCTAAGGCCACAC

TGCAAGATATTGTCCTCCATCTCGAACCCCAGAATGAGATACCAGTGGACCTTCT

GGGCCACGGACAGTTGTCCGATAGCGAGGAGGAAAACGACGAAATCGACGGTGT

TAACCACCAGCACTTGCCGGCTCGGAGGGCAGAGCCCCAGAGACATACCATGCT

GTGCATGTGTTGCAAAGCTAGTAGCAGCGTGAGCCCCACCACCAGCGTGCACCC

CACCCCCACCAGCGTGCCCCCCACCCCCACCAAGAGCAGCCCCGCTAGCTGA
```

Example 2—Recombinant Fusion Proteins of Anti-DC Receptors (DCRs), TLR Ligands, and HPV Sequences Below is an example of a TLR2 ligand (tri-acylated cohesin, expressed in *E. coli*) where the C residue in the D1 leader domain is lipidated, this can be non-covalently attached to anti-CD40-HPV vaccine when the anti-CD40 has, e.g., a Dockerin domain fused to either the C-terminus or the L chain or the H chain C-terminus distal to the HPV E6/7 sequences.

```
D1-6His-Cohesin-Nhe-Spe-Not (note that additional cancer
antigen sequences can be added distal to the Cohesin domain)
                                          (SEQ ID NO: 23)
MKKLLIAAMMAAALAACSQEAKQEVKEAVQAVESDVKDTAMGSSHHHHHHSSGL

VPRGSHMASMDLDAVRIKVDTVNAKPGDTVNIPVRFSGIPSKGIANCDFVYSYDPNV

LEIIEIKPGELIVDPNPTKSFDTAVYPDRKMIVFLFAEDSGTGAYAITKDGVFATIVAK

VKEGAPNGLSVIKFVEVGGFANNDLVEQKTQFFDGGVNVGDTTEPATPTTPVTTPTT

TDDLDAASLIKTSEF
```

D1-6His-Cohesin-Nhe-Spe-Not DNA sequence
(SEQ ID NO: 24)
ATGAAAAAACTGCTGATTGCCGCCATGATGGCTGCAGCTCTGGCCGCA

TGCAGCCAGGAAGCCAAACAGGAAGTGAAAGAAGCCGTGCAGGCCGTG

GAAAGCGATGTGAAAGATACCGCCATGGGCAGCAGCCATCATCATCAT

CATCACAGCAGCGGCCTGGTGCCGCGCGGCAGCCATATGGCTAGTATG

GATCTGGATGCAGTAAGGATTAAAGTGGACACAGTAAATGCAAAACCG

GGAGACACAGTAAATATACCTGTAAGATTCAGTGGTATACCATCCAAG

GGAATAGCAAACTGTGACTTTGTATACAGCTATGACCCGAATGTACTT

GAGATAATAGAGATAAAACCGGGAGAATTGATAGTTGACCCGAATCCT

ACCAAGAGCTTTGATACTGCAGTATATCCTGACAGAAAGATGATAGTA

TTCCTGTTTGCGGAAGACAGCGGAACAGGAGCGTATGCAATAACTAAA

GACGGAGTATTTGCTACGATAGTAGCGAAAGTAAAAGAAGGAGCACCT

AACGGGCTCAGTGTAATCAAATTTGTAGAAGTAGGCGGATTTGCGAAC

AATGACCTTGTAGAACAGAAGACACAGTTCTTTGACGGTGGAGTAAAT

GTTGGAGATACAACAGAACCTGCAACACCTACAACACCTGTAACAACA

CCGACAACAACAGATGATCTAGATGCAGCTAGCTTAATTAAAACTAGT

GAATTCTGA

Below is an example of an anti-CD40 L chain bearing a preferred TLR5L Flagellin domain (shown underlined). This would be co-transfected with the matching H chain bearing HPV E6/7 antigen at the C-terminus.

hAnti-CD40VK2-LV-hIgGK-C-Flgn1-Flgn2
(SEQ ID NO: 25)
DIQMTQSPSSLSASVGDRVTITCSASQGISNYLNWYQQKPGKAVKLLIYYTSILHSGV
PSRFSGSGSGTDYTLTISSLQPEDFATYYCQQFNKLPPTFGGGTKLEIKRTVAAPSVFIF
PPSDEQLKSGTASVVCLLNNFYPREAKVQWKVDNALQSGNSQESVTEQDSKDSTYS
LSSTLTLSKADYEKHKVYACEVTHQGLSSPVTKSFNRGECASIERLSSGLRINSAKDD
AAGQAIANRFTANIKGLTQASRNANDGISIAQTTEGALNEINNNLQRVRELAVQSAN
STNSQSDLDSIQAEITQRLNEIDRVSGQTQFNGVKVLAQDNTLTIQVGANDGETIDIDL
KQINSQTLGLDSLNVQASQPELAEAAAKTTENPLQKIDAALAQVDALRSDLGAVQN
RFNSAITNLGNTVNNLSEARSRIEDSDYATEVSNMSRAQILQAS
(underlined sequence is Flagellin domain)

hAnti-CD40VK2-LV-hIgGK-C-Flgn1-Flgn2 DNA sequence
(SEQ ID NO: 26)
ATGAGGGTCCCCGCTCAGCTCCTGGGGCTCCTGCTGCTCTGGCTCCCAGGCGCGC
GATGTGATATCCAGATGACACAGAGCCCTTCCTCCCTGTCTGCCTCTGTGGGAGA
CAGAGTCACCATCACCTGCAGTGCAAGTCAGGGCATTAGCAATTATTTAAACTGG
TATCAGCAGAAACCAGGCAAGGCCGTTAAACTCCTGATCTATTACACATCAATTT
TACACTCAGGAGTCCCATCAAGGTTCAGTGGCAGTGGGTCTGGGACAGATTATAC
CCTCACCATCAGCTCCCTGCAGCCTGAAGATTTCGCCACTTACTATTGTCAGCAG
TTTAATAAGCTTCCTCCGACGTTCGGTGGAGGCACCAAACTCGAGATCAAACGAA
CTGTGGCTGCACCATCTGTCTTCATCTTCCCGCCATCTGATGAGCAGTTGAAATCT
GGAACTGCCTCTGTTGTGTGCCTGCTGAATAACTTCTATCCCAGAGAGGCCAAAG
TACAGTGGAAGGTGGATAACGCCCTCCAATCGGGTAACTCCCAGGAGAGTGTCA
CAGAGCAGGACAGCAAGGACAGCACCTACAGCCTCAGCAGCACCCTGACGCTGA
GCAAAGCAGACTACGAGAAACACAAAGTCTATGCCTGCGAAGTCACCCATCAGG
GCCTGAGCTCGCCCGTCACAAAGAGCTTCAACAGGGGAGAGTGTGCTAGTATCG
AGCGTCTGTCTTCTGGTCTGCGTATCAACAGCGCGAAAGACGATGCGGCAGGTCA
GGCGATTGCTAACCGTTTTACCGCGAACATCAAAGGTCTGACTCAGGCTTCCCGT
AACGCTAACGACGGTATCTCCATCGCGCAGACCACTGAAGGCGCGCTGAACGAA
ATCAACAACAACCTGCAGCGTGTGCGTGAACTGGCGGTTCAGTCTGCTAACAGC
ACTAACTCCCAGTCTGACCTCGACTCCATCCAGGCTGAAATCACCCAGCGCCTGA -continued

```
ACGAAATCGACCGTGTATCCGGTCAGACTCAGTTCAACGGCGTGAAAGTCCTGG

CGCAGGACAACACCCTGACCATCCAGGTTGGTGCCAACGACGGTGAAACTATCG

ATATCGATCTGAAGCAGATCAACTCTCAGACCCTGGGCCTGGATTCACTGAACGT

GCAGGCTAGTCAACCAGAGCTGGCGGAAGCAGCCGCTAAAACCACCGAAAACCC

GCTGCAGAAAATTGATGCCGCGCTGGCGCAGGTGGATGCGCTGCGCTCTGATCTG

GGTGCGGTACAAAACCGTTTCAACTCCGCTATCACCAACTTGGGCAATACCGTAA

ACAACCTGTCTGAAGCGCGTAGCCGTATCGAAGATTCCGACTACGCGACCGAAG

TTTCCAACATGTCTCGCGCGCAGATTCTGCAGGCTAGCTGA
```

Below is an example of analogous HPV 18 E6/7 sequences fused to DC-targeting antibody H chain (in this case anti-Langerin). This can be fused instead to the H chain of the preferred antiCD40 antibody in place of the HPV 16 sequences, or fused downstream of the HPV 16 sequences, or fused to the anti-CD40 L chain—in each case making a vaccine bearing both HPV 16 and HPV 18 sequences.

```
Anti-Langerin 15B10H-LV-hIgG4H-C-HPV18E7-HPV18E6-f1
                                     (SEQ ID NO: 27)
QVQLRQSGPELVKPGASVKMSCKASGYTFTDYVISWVKQRTGQGLEWIGDIYPGSG

YSFYNENFKGKATLTADKSSTTAYMQLSSLTSEDSAVYFCATYYNYPFAYWGQGTL

VTVSAAKTTGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYGPPCPPCPA

PEFEGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKAS*MHGPKATLQ*

*DIVLHLEPQNEIPVDLLGHGQLSDSEEENDEIDGVNHQHLPARRAEPQRHTMLCMC*

*CK*ASMARFEDPTRRPYKLPDLCTELNTSLQDIEITCVYCKTVLELTEVGEFAFKDLFV

VYRDSIPHAACHKCIDFYSRIRELRHYSDSVYGDTLEKLTNTGLYNLLIRCLRCQKPL

NPASSSVSPTTSVHPTPTSVPPTPTKSSPAS
(Bold, italicized single underline sequence is HPV18 E6; bold, italicized
double underline sequence is HPV18 E7; non-bolded, non-italicized double
underlined (f1) sequence is a flexible glycosylated linker sequence)

Anti-Langerin 15B10H-LV-hIgG4H-C-HPV18E7-HPV18E6-f1 DNA sequence
                                     (SEQ ID NO: 28)
ATGGAATGGAGGATCTTTCTCTTCATCCTGTCAGGAACTGCAGGTGTCCACTCCC

AGGTTCAGCTGCGGCAGTCTGGACCTGAGCTGGTGAAGCCTGGGGCTTCAGTGA

AGATGTCCTGCAAGGCTTCTGGATACACATTTACTGACTATGTTATAAGTTGGGT

GAAGCAGAGAACTGGACAGGGCCTTGAGTGGATTGGAGATATTTATCCTGGAAG

TGGTTATTCTTTCTACAATGAGAACTTCAAGGGCAAGGCCACACTGACTGCAGAC

AAATCCTCCACCACAGCCTACATGCAGCTCAGCAGCCTGACATCTGAGGACTCTG

CGGTCTATTTCTGTGCAACCTACTATAACTACCCTTTTGCTTACTGGGGCCAAGGG

ACTCTGGTCACTGTCTCTGCAGCCAAAACAACGGGCCCATCCGTCTTCCCCCTGG

CGCCCTGCTCCAGGAGCACCTCCGAGAGCACAGCCGCCCTGGGCTGCCTGGTCA

AGGACTACTTCCCCGAACCGGTGACGGTGTCGTGGAACTCAGGCGCCCTGACCA
```

```
                        -continued
GCGGCGTGCACACCTTCCCGGCTGTCCTACAGTCCTCAGGACTCTACTCCCTCAG

CAGCGTGGTGACCGTGCCCTCCAGCAGCTTGGGCACGAAGACCTACACCTGCAA

CGTAGATCACAAGCCCAGCAACACCAAGGTGGACAAGAGAGTTGAGTCCAAATA

TGGTCCCCCATGCCCACCCTGCCCAGCACCTGAGTTCGAAGGGGGACCATCAGTC

TTCCTGTTCCCCCCAAAACCCAAGGACACTCTCATGATCTCCCGGACCCCTGAGG

TCACGTGCGTGGTGGTGGACGTGAGCCAGGAAGACCCCGAGGTCCAGTTCAACT

GGTACGTGGATGGCGTGGAGGTGCATAATGCCAAGACAAAGCCGCGGGAGGAG

CAGTTCAACAGCACGTACCGTGTGGTCAGCGTCCTCACCGTCCTGCACCAGGACT

GGCTGAACGGCAAGGAGTACAAGTGCAAGGTCTCCAACAAAGGCCTCCCGTCCT

CCATCGAGAAAACCATCTCCAAAGCCAAAGGGCAGCCCCGAGAGCCACAGGTGT

ACACCCTGCCCCCATCCCAGGAGGAGATGACCAAGAACCAGGTCAGCCTGACCT

GCCTGGTCAAAGGCTTCTACCCCAGCGACATCGCCGTGGAGTGGGAGAGCAATG

GGCAGCCGGAGAACAACTACAAGACCACGCCTCCCGTGCTGGACTCCGACGGCT

CCTTCTTCCTCTACAGCAGGCTAACCGTGGACAAGAGCAGGTGGCAGGAGGGGA

ATGTCTTCTCATGCTCCGTGATGCATGAGGCTCTGCACAACCACTACACACAGAA

GAGCCTCTCCCTGTCTCTGGGTAAAGCTAGTATGCACGGGCCTAAGGCCACACTG

CAAGATATTGTCCTCCATCTCGAACCCCAGAATGAGATACCAGTGGACCTTCTGG

GCCACGGACAGTTGTCCGATAGCGAGGAGGAAAACGACGAAATCGACGGTGTTA

ACCACCAGCACTTGCCGGCTCGGAGGGCAGAGCCCCAGAGACATACCATGCTGT

GCATGTGTTGCAAAGCTAGTATGGCCAGATTCGAGGATCCAACACGCCGACCTTA

CAAATTGCCGGACCTTTGCACGGAGCTGAACACTTCCCTGCAGGACATAGAAATT

ACCTGCGTCTACTGCAAGACCGTTCTCGAACTGACAGAAGTAGGCGAGTTTGCGT

TTAAAGATCTGTTCGTGGTGTATCGGGATAGCATTCCCCACGCAGCTTGTCATAA

GTGTATCGACTTCTATTCTAGGATCCGGGAGCTCAGACACTATAGCGATTCCGTG

TACGGCGACACACTTGAGAAGCTCACTAACACCGGGCTGTACAACCTCCTGATCC

GGTGCTTGAGGTGTCAGAAACCCTGAATCCTGCTAGTAGCAGCGTGAGCCCCAC

CACCAGCGTGCACCCCACCCCCACCAGCGTGCCCCCCACCCCCACCAAGAGCAG

CCCCGCTAGCTGA
```

Example 3—CD40 Targeting HPV Vaccine (CD40HVac)

Figures 8A, 8B:
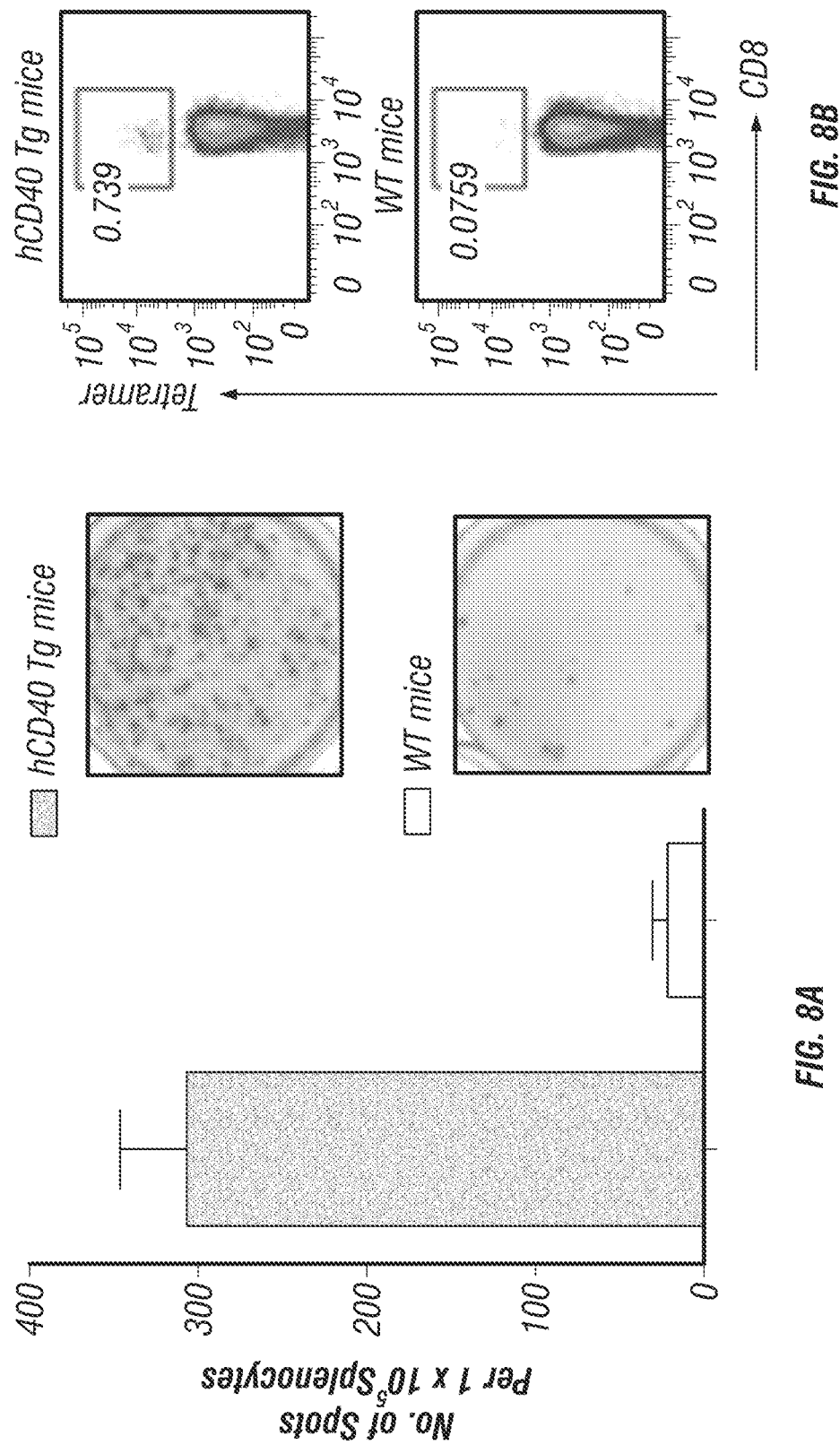
FIGS. 8A-8B: CD40HVac plus poly IC induces E6/7-specific CD8+ T cells in hCD40 transgenic animals.

CD40HVac plus poly IC induces E6/7-specific CD8+ CTLs in human CD40 transgenic B6 (hCD40Tg) mice. hCD40Tg and WT animals (5 mice/group) were immunized subcutaneously (SC) with 30 µg CD40HVac plus 50 µg poly IC in PBS (100 µl) and boosted twice two weeks apart. The amounts of CD40HVac and poly IC were predetermined in separate experiments. Seven days after the second boosting, IFNγ ELISPOT was performed using purified CD8+ T cells from spleens (FIG. 8a). Compared to WT mice, hCD40Tg mice elicited increased numbers of CD8+IFNγ+ T cells. The inventors also observed that hCD40Tg mice had increased E7-specific CD8+ T cells in the blood, as measured by tetramer staining (FIG. 8b). In addition, CD40HVac plus poly IC induced greater levels of E6/7-specific CD4+ T cell responses in hCD40Tg mice than in WT animals (not shown). Taken together, the inventors concluded that CD40HVac targets human CD40 in vivo and can thus elicit E6/7-specific cellular responses. The inventors also found that CD40HVac plus poly IC (adjuvant) was more potent than CD40HVac alone at eliciting E6/7-specific T cell responses in hCD40Tg mice (data not shown), although humanized anti-CD40 antibody used in CD40HVac has an agonistic property.

Figure 9A:
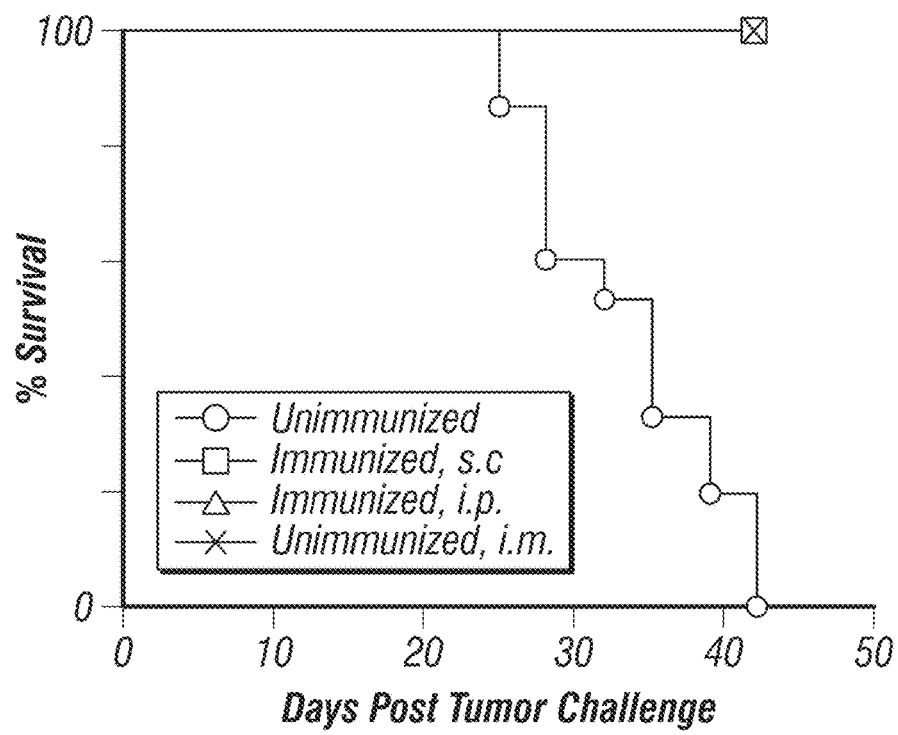
FIG. 9: CD40HVac plus poly IC induces therapeutic immunity in hCD40Tg mice. (a) Survival curves. 10 mice per group. (b) TC-1 tumor progression. 10 mice per group.
Figure 9B:
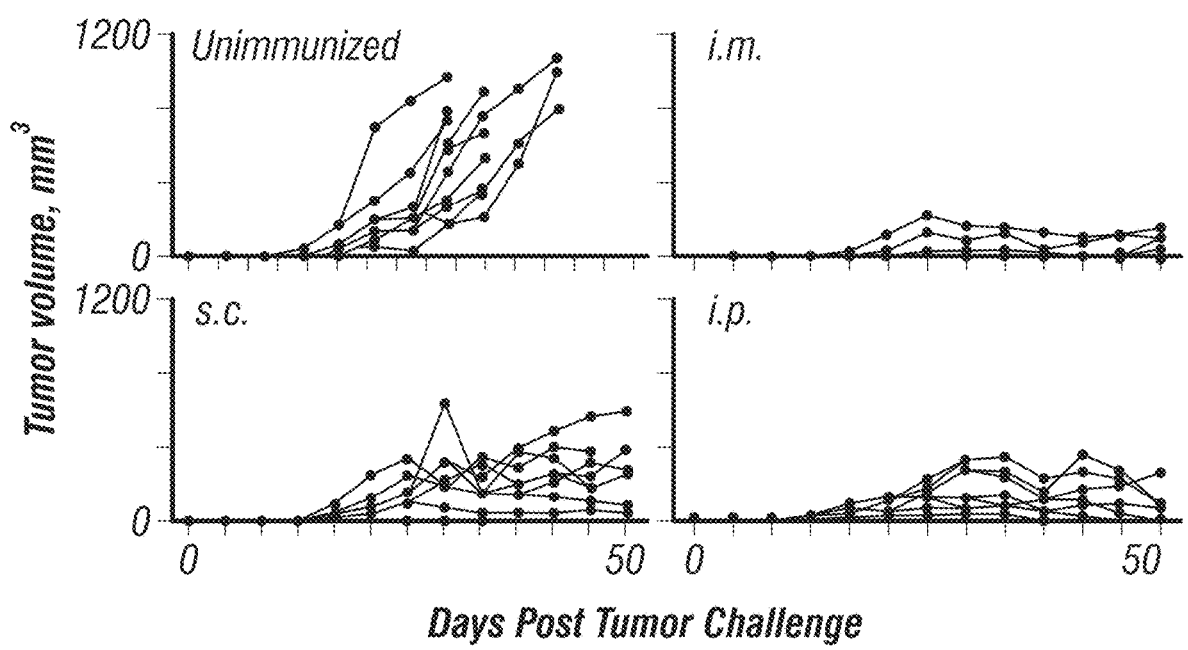

CD40HVac plus poly IC can mount therapeutic immunity in hCD40Tg animals. hCD40Tg mice (10 mice per group) were SC challenged with HPV E6/7-expressing TC-1 tumor cells ($5 \times 10^4$). The inventors confirmed that animals harbor palpable tumors on day 6 after TC-1 challenge. Animals were then immunized SC, intramuscularly (IM), or intraperitoneally (IP) with 30 µg CD40HVac plus 50 µg poly IC on days 6, 12, and 24. A control group was kept without immunization. FIG. 9a shows that all animals receiving CD40HVac plus poly IC survived while all control animals died. Injection of poly IC alone did not promote survival (data not shown). In a separate experiment, we measured progression of TC-1 tumors by assessing tumor volume (FIG. 9b). All control animals (10 mice) developed tumors and died within 40 days of TC-1 challenge. In contrast, CD40HVac plus poly IC treatment suppressed tumor progression. It is also of note that some of the treated animals developed large tumors (200-600 mm$^3$), and these tumors regressed over time during vaccination. Taken together, the inventors concluded that CD40HVac elicits therapeutic immunity in hCD40Tg mice. Furthermore, the data indicated that the route of immunization is an important factor that could impact the overall therapeutic efficacy of the CD40HVac regimen.

Figure 10:
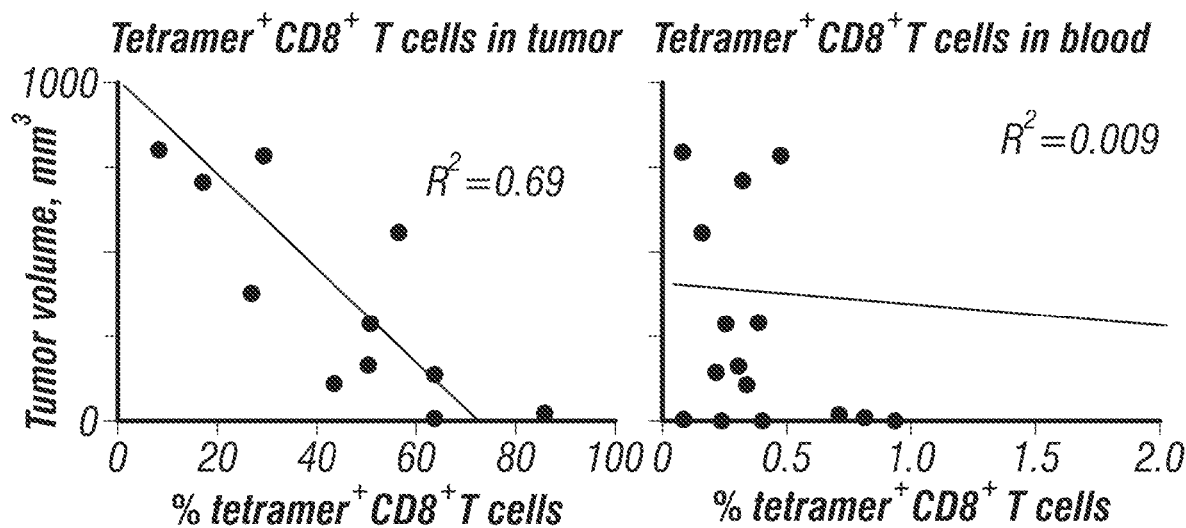
FIG. 10: The percentage of E7-specific tetramer+CD8+ T cells in tumors, but not blood, inversely correlates with tumor volume.

CD8+ CTL infiltration into tumors is critical for tumor regression. Human CD40 transgenic (hCD40Tg) mice were SC challenged with high numbers of TC-1 tumor cells ($2 \times 10^5$ cells). Animals were then immunized with 30 μg CD40HVac plus 50 μg poly IC on days 6 and 12. Without vaccination, all animals died within 25 days after the tumor challenge. On day 60, the percentages of H2-db (RAHYNIVTF) tetramer+CD8+ T cells in tumors and blood were assessed (FIG. 10). The percentage of tetramer+CD8+ T cells in the tumor (left) inversely correlates with tumor volume. There was no such correlation between the percentage of tetramer+CD8+ T cells in the blood (right) or spleen (not shown) and the tumor volume. Thus, infiltration of antigen-specific CD8+ CTLs into tumors is critical for tumor regression. Thus, we anticipate the improvement of CD40HVac efficacy by promoting effector cell infiltration into and retention within mucosal tumors.

Figure 11A:
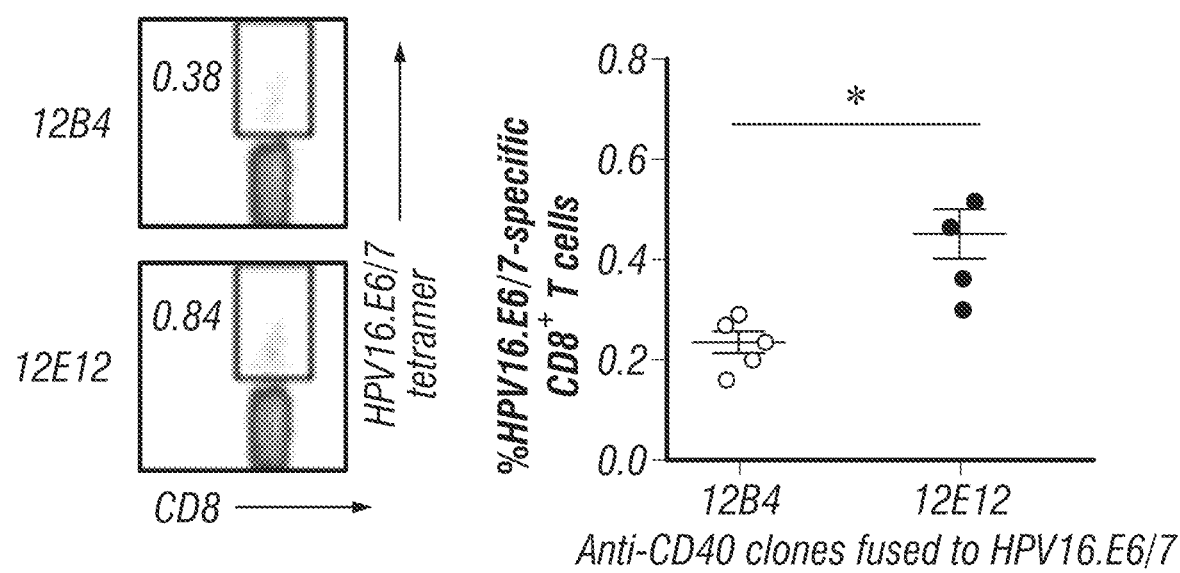
FIG. 11: CD40HVac made with anti-CD40 (clone 12E12) is more efficient than that made with anti-CD40 (clone 12B6) at inducing E6/7-specific CD8+ T cell responses.
Figure 11B:
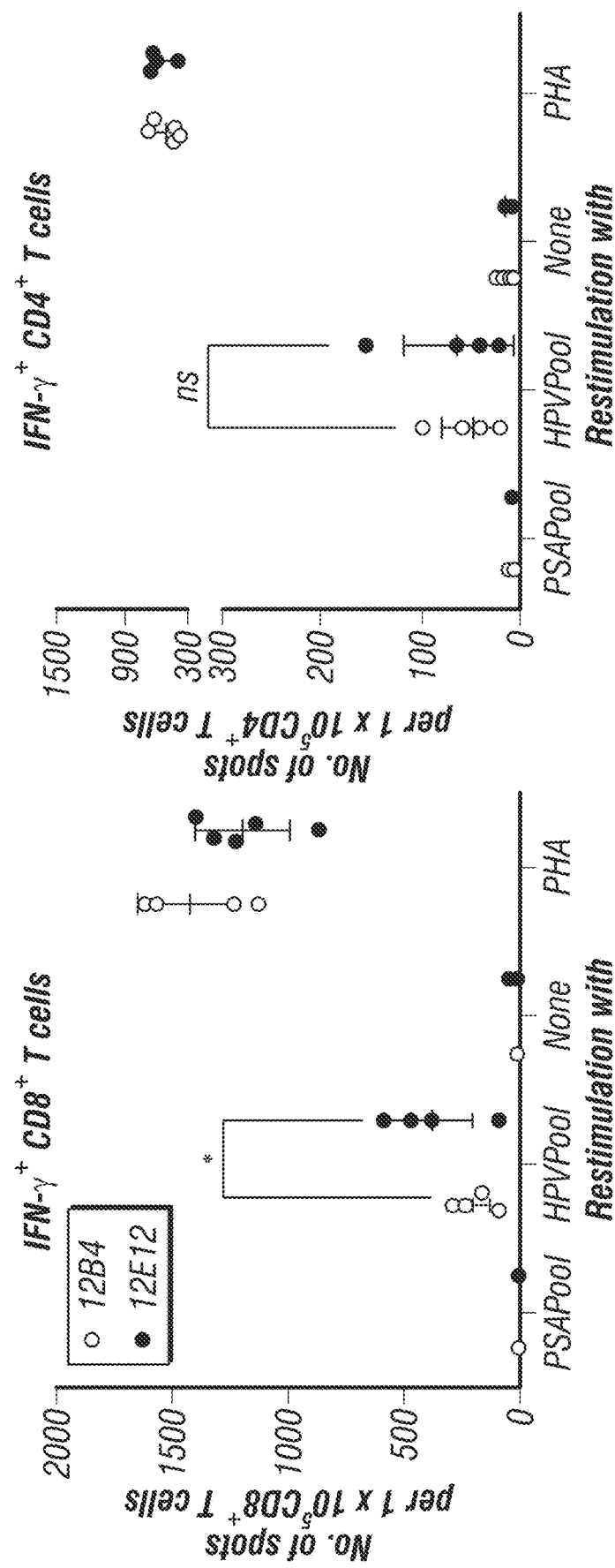

CD40HVac made with anti-CD40 (12E12 clone) is more efficient than CD40HVac made with anti-CD40 (12B4 clone) at eliciting HPV16.E6/7-specific CD8+ T cell responses. The inventors compared recombinant fusion proteins made with three different clones of anti-CD40 mAbs (12E12 and 12B4) for their ability to prime HPV16.E6/7-specific CD8+ T cell responses. The inventors used poly IC as an adjuvant. hCD40Tg animals received three doses of recombinant fusion proteins (30 μg/dose) plus poly IC (50 μg/dose) via s.c. Seven days after the third immunization, the percentage of E7-specific CD8+ T cells in the blood were determined by tetramer staining. As shown in left panel of FIG. 11a, recombinant fusion proteins made with 12E12 was more efficient than those made with 12B4 clone at inducing E6/7-specific CD8+ T cell responses. The inventors also found that anti-CD40 (12E12)-HPV16.E6/7 was more efficient than anti-CD40 (12B6)-HPV16.E6/7 at eliciting IFNγ+ CD8+ T cell responses by ELISPOT assay using splenocytes (left panel in FIG. 11b). HPV16.E6/7 fused with the two clones of anti-CD40 mAbs resulted in similar levels of E6/7-specific IFNγ+CD4+ T cell responses (right panel in FIG. 11b).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

*Antibodies: A Laboratory Manual*, Cold Spring Harbor Laboratory, 1988
Atherton et al., 1985
Ausubel et al., 1996
Barany and Merrifield, 1979
Bird et al., 1988
Burke et al., 1994
Cumber et al., 1992
Dholakia et al., 1989
Epitope Mapping Protocols (1996)
Glennie et al., 1987
Goding, 1986, pp. 60 61
Holliger et al, 1993
Holliger & Winter, 1999
Holt et al., 2003
Hu et al. 1996
Huston et al., 1988
Khatoon et al., 1989
King et al., 1989
Kohl et al., 2003
Kyte and Doolittle, 1982
Liu et al., 2003
McCafferty et al., 1990
Merchand et al., 1998
Merrifield, 1986
O'Shannessy et al., 1987
Owens & Haley, 1987
Pack, et al., 1992
Potter & Haley, 1983
Reiter et al., 1996
Repp et al., 1995
Ridgeway et al., 1996
Sambrook et al., 2001
Skerra, 2000
Skerra, 2001
Staerz & Bevan, 1986
Stewart and Young, 1984
Tam et al., 1983
Tigges et al., 1996
Ward, 1989
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,277,437
U.S. Pat. No. 4,275,149
U.S. Pat. No. 4,366,241
U.S. Pat. No. 4,472,509
U.S. Pat. No. 4,554,101
U.S. Pat. No. 4,879,236
U.S. Pat. No. 4,938,948
U.S. Pat. No. 5,196,066
U.S. Pat. No. 5,741,957
U.S. Pat. No. 5,750,172
U.S. Pat. No. 5,756,687
U.S. Pat. No. 5,827,690
U.S. Pat. No. 5,871,986
U.S. Pat. No. 6,091,001
U.S. Pat. No. 6,651,655

U.S. Patent Publication No. 2005/0106660
U.S. Patent Publication No. 2006/0058510
U.S. Patent Publication No. 2006/0088908
U.S. Patent Publication No. 2010/0285564
U.S. Patent Publication No. 2012/0039,916
U.S. Patent Publication No. 2012/023,102
U.S. Provisional Patent No. 61/332,465
U.S. patent application Ser. No. 12/024,036
U.S. patent application Ser. No. 12/024,897
U.S. patent application Ser. No. 12/025,010
U.S. patent application Ser. No. 12/026,095
U.S. patent application Ser. No. 12/036,138
U.S. patent application Ser. No. 12/036,158
U.S. patent application Ser. No. 12/504,463
U.S. patent application Ser. No. 12/717,778
U.S. patent application Ser. No. 12/717,789
U.S. patent application Ser. No. 12/717,804
U.S. patent application Ser. No. 12/718,365
U.S. patent application Ser. No. 12/882,052
U.S. patent application Ser. No. 13/100,684
U.S. patent application Ser. No. 13/208,993
U.S. patent application Ser. No. 13/269,951
U.S. patent application Ser. No. 13/282,112
U.S. patent application Ser. No. 13/415,564
U.S. patent application Ser. No. 13/424,582
U.S. patent application Ser. No. 13/430,206
U.S. patent application Ser. No. 13/594,397
U.S. patent application Ser. No. 13/596,526
U.S. patent application Ser. No. 13/465,371
U.S. patent application Ser. No. 13/397,932
PCT Publication No. WO2006/056464
PCT Publication No. WO94/13804
PCT Publication No. WO 2008/103947
PCT Publication No. WO 2008/103953
PCT Publication No. WO 2008/118587
PCT Publication No. WO 2010/104747
PCT Publication No. WO 2010/104749
PCT Publication No. WO 2010/104761
PCT Publication No. WO 2012/021834
PCT Patent Application No. PCT/US92/09965
PCT Patent Application No. PCT/US13/72217
PCT Patent Application No. PCT/US2013/05839

What is claimed is:

1. A fusion protein comprising an anti-CD40 antibody or fragment thereof, comprising at least three complementarity determining regions (CDRs) from each of a heavy and light chain of an anti-CD40 antibody, at least one peptide linker and at least one human papillomavirus (HPV) E6 antigen and at least one HPV E7 antigen,
   wherein the E6 and E7 antigens comprise an antigen with at least 90% sequence identity to SEQ ID NO:1 and an antigen with at least 90% sequence identity to SEQ ID NO:2; and
   wherein the fusion protein comprises an amino acid sequence that has at least 95% sequence identity to SEQ ID NO:19.

2. The fusion protein of claim 1, wherein the anti-CD40 antibody or fragment thereof is humanized.

3. The fusion protein of claim 1, wherein the fusion protein comprises peptide linkers comprising the amino acid sequences of SEQ ID NO:5 and SEQ ID NO:6.

4. A fusion protein comprising an anti-CD40 antibody or fragment thereof, comprising at least three complementarity determining regions (CDRs) from each of a heavy and light chain of an anti-CD40 antibody, at least one peptide linker and at least one human papillomavirus (HPV) E6 antigen and at least one HPV E7 antigen,
   wherein the E6 and E7 antigens comprise an antigen with at least 90% sequence identity to SEQ ID NO:3 and an antigen with at least 90% sequence identity to SEQ ID NO:4; and
   wherein the fusion protein comprises an amino acid sequence that has at least 95% sequence identity to SEQ ID NO:21.

5. The fusion protein of claim 1, wherein the three CDRs from the heavy chain of the anti-CD40 antibody comprises the amino acid sequences of SEQ ID NOs:14-16, and wherein the three CDRs from the light chain of the anti-CD40 antibody comprises the amino acid sequences of SEQ ID NOs:11-13.

6. A method of making a fusion protein according claim 1 comprising isolating the fusion protein from a recombinant host cell expressing the fusion protein.

7. A method for inducing an immune response to at least one HPV epitope comprising administering to a patient a composition comprising the fusion protein of claim 1.

8. The method of claim 7, wherein the anti-CD40 antibody or fragment thereof comprises an anti-CD40 antibody light chain variable region comprising a CDR1, CDR2, and CDR3 of SEQ ID Nos:11-13, respectively, and an anti-CD40 antibody heavy chain variable region comprising a CDR1, CDR2, and CDR3 of SEQ ID Nos:14-16, respectively.

9. The method of claim 7, wherein the anti-CD40 antibody or fragment thereof is humanized.

10. The method of claim 7, wherein the composition further comprises an adjuvant.

11. The method of claim 7, further comprising administering to the patient a separate HPV vaccine.

12. The method of claim 11, wherein the separate HPV vaccine is Gardasil™ or Cervarix™.

13. The fusion protein of claim 4, wherein the anti-CD40 antibody or fragment thereof is humanized.

14. The fusion protein of claim 4, wherein the fusion protein comprises peptide linker or linkers comprising the amino acid sequences of SEQ ID NO:5 and SEQ ID NO:6.

15. The fusion protein of claim 4, wherein the three CDRs from the heavy chain of the anti-CD40 antibody comprises the amino acid sequences of SEQ ID NOs:14-16, and wherein the three CDRs from the light chain of the anti-CD40 antibody comprises the amino acid sequences of SEQ ID NOs:11-13.

16. A method of making a fusion protein according claim 4 comprising isolating the fusion protein from a recombinant host cell expressing the fusion protein.

17. A method for inducing an immune response to at least one HPV epitope comprising administering to a patient a composition comprising the fusion protein of claim 4.

18. The method of claim 17, wherein the anti-CD40 antibody or fragment thereof comprises an anti-CD40 antibody light chain variable region comprising a CDR1, CDR2, and CDR3 of SEQ ID Nos:11-13, respectively, and an anti-CD40 antibody heavy chain variable region comprising a CDR1, CDR2, and CDR3 of SEQ ID Nos:14-16, respectively.

19. The method of claim 17, wherein the anti-CD40 antibody or fragment thereof is humanized.

20. The method of claim 17, wherein the composition further comprises an adjuvant.

21. The method of claim 17, further comprising administering to the patient a separate HPV vaccine.

22. The method of claim 21, wherein the separate HPV vaccine is Gardasil™ or Cervarix™.

* * * * *